US008748179B2

(12) United States Patent
Egusa et al.

(10) Patent No.: US 8,748,179 B2
(45) Date of Patent: Jun. 10, 2014

(54) METHOD FOR EFFICIENT PRODUCTION OF INDUCED PLURIPOTENT STEM CELLS UTILIZING CELLS DERIVED FROM ORAL MUCOSA

(75) Inventors: Hiroshi Egusa, Osaka (JP); Hirofumi Yatani, Osaka (JP); Hiroki Kayashima, Osaka (JP)

(73) Assignee: Osaka University, Osaka (JP)

( * ) Notice: Subject to any disclaimer, the term of this patent is extended or adjusted under 35 U.S.C. 154(b) by 0 days.

(21) Appl. No.: 13/393,080

(22) PCT Filed: Jun. 23, 2010

(86) PCT No.: PCT/JP2010/060680
§ 371 (c)(1),
(2), (4) Date: Feb. 28, 2012

(87) PCT Pub. No.: WO2011/024550
PCT Pub. Date: Mar. 3, 2011

(65) Prior Publication Data
US 2012/0156778 A1    Jun. 21, 2012

(30) Foreign Application Priority Data
Aug. 31, 2009  (JP) ................................ 2009-200932

(51) Int. Cl.
*C12N 5/00*   (2006.01)
*C12N 5/02*   (2006.01)
*C12N 15/00*  (2006.01)
*C12N 5/071*  (2010.01)
*A01N 63/00*  (2006.01)
*A61K 48/00*  (2006.01)

(52) U.S. Cl.
USPC ........... 435/377; 435/325; 435/366; 435/354; 435/320.1; 424/93.21

(58) Field of Classification Search
CPC ... A61K 35/37; A61L 27/3834; C12N 5/0696
USPC ...................... 435/377, 325, 366, 354, 320.1; 424/93.21
See application file for complete search history.

(56) References Cited

U.S. PATENT DOCUMENTS

| 8,048,999 B2 | 11/2011 | Yamanaka et al. |
| 2009/0047263 A1 | 2/2009 | Yamanaka et al. |

FOREIGN PATENT DOCUMENTS

| JP | 4183742 | 9/2008 |
| WO | 2007/001016 | 1/2007 |
| WO | 2007/069666 | 6/2007 |
| WO | 2008/017927 | 2/2008 |
| WO | 2009/093022 | 7/2009 |
| WO | 2010013359 | 2/2010 |

OTHER PUBLICATIONS

Stadtfeld. Science, 322: 945-949, 2008.*
Okita. Science, 322: 949-953, 2008.*
Gonzalez. PNAS, 106(22): 8918-8922, 2009.*
Hanley et al., British Journal of Hæmatology, 151: 16-24, 2010.*
Oliveri et al. Regenerative Medicine, 2(5): 795-816, Sep. 2007.*
Djuric and Ellis, 202, Stem Cell Research and Therapy, 2010,1:3.*
Kim et al. Cell Stem Cell, 4(6): 472-476, 2009.*
Miyamoto. Biology of Reproduction, 80: 935-943, 2009.*
Wade et al. Eur. J. Biochem., 269:2284-2287, 2002.*
Gurdon & Colman. Nature, 402:743-746, 1999.*
Takahashi et al., Cell, 131: 861-872, Nov. 2007.*
Saczko et al., Folia Histochemica et Cytobiologica, 46(1): 117-119, Jan. 1, 2008.*
International Search Report for PCT/JP2010/060680, dated Aug. 24, 2010.
Yan, X. et al., iPS Cells Reprogrammed From Human Mesenchymal-Like Stem/Progenitor Cells of Dental Tissue Origin, Stem Cells and Development, 2010, vol. 19, No. 4, pp. 469-480.
Lin, N.H. et al., Stem Cells and Future Periodontal Regeneration, Periodontology 2000, 2009, vol. 51, No. 1, pp. 239-251.
Supplementary European Search Report dated Oct. 25, 2013 for EP Patent Application No. 10811601.3.
Yamanaka, S., A fresh look at iPS cells, Cell, 2009, vol. 137, Issue 1, pp. 13-17.
Nakagawa, M. et al., Generation of induced pluripotent stem cells without Myc from mouse and human fibroblasts, Nature Biotechnology, 2008, vol. 26, No. 1, pp. 101-106.
Osaka University launches research to generate iPS cells from human gingiva, Nikkan Kogyo Shinbun—Distribution Service Newspaper, 2010, p. 22.
Miyoshi, K. et al., Generation of human induced pluripotent stem cells from oral mucosa, Journal of Bioscience and Bioengineering, 2010, vol. 110, No. 3, pp. 345-350.
Tamaoki, N. et al., Induction of pluripotent stem cells from human dental pulp stem cells, 81st Annual Meeting of the Japanese Biochemical Society, 31st Annual Meeting of the Molecular Biology Society of Japan Godo Taikai Program Koen Yoshishu, 2008, 1T25-12.
Tezuka, K., Shihai kansaibo kara no iPS saibo yudo to bank-ka eno tenbo, Regenerative Medicine, 2009, vol. 8, Suppl., p. 75, SY-1-5.
Oda, Y. et al., Shihai (oyashirazu) saibo kara no iPS saibo no juritsu, Regenerative Medicine, 2009, vol. 8, Suppl., p. 253, P-130.
Yamada, Y. et al., Injectable tissue-engineered bone using autogenous bone marrow-derived stromal cells for maxillary sinus augmentation: clinical application report from a 2-6-year follow-up, Tissue Eng. Part A, 2008, vol. 14, No. 10, pp. 1699-707 (Abstract only).
Aoi, T. et al., Generation of pluripotent stem cells from adult mouse liver and stomach cells, Science, 2008, vol. 321, pp. 699-702.
Loh, Y.H. et al., Generation of induced pluripotent stem cells from human blood, Blood, 2009, vol. 113, No. 22, pp. 5476-5479.
Nozaki, T., Tooth regeneration by pluripotent stem cells, Seibutsu-kogaku Kaishi, vol. 86, No. 5, p. 244, 2008.

* cited by examiner

*Primary Examiner* — Thaian N Ton
(74) *Attorney, Agent, or Firm* — Roylance, Abrams, Berdo & Goodman, L.L.P.

(57) ABSTRACT

A main object of the present invention is to provide a technique to produce iPS cells with less burden on the patient and with high establishment efficiency. iPS cells can be efficiently produced with significantly improved establishment efficiency by selecting cells derived from oral mucosa and introducing, into the cells, reprogramming factors capable of inducing the cells into pluripotent stem cells.

2 Claims, 17 Drawing Sheets

Bone Differentiation Induction Medium (Day 28)
Alkaline Phosphatase and Von Kossa Double Staining Three-Factor Transduction Four-Factor Transduction

SEQUENCE LISTING

<160> NUMBER OF SEQ ID NOS: 30

<210> SEQ ID NO 1
<211> LENGTH: 24
<212> TYPE: DNA
<213> ORGANISM: Artificial Sequence
<220> FEATURE:
<223> OTHER INFORMATION: chemically synthesized primer

<400> SEQUENCE: 1
agggtctgct actgagatgc tctg                                          24

<210> SEQ ID NO 2
<211> LENGTH: 24
<212> TYPE: DNA
<213> ORGANISM: Artificial Sequence
<220> FEATURE:
<223> OTHER INFORMATION: chemically synthesized primer

<400> SEQUENCE: 2
caaccactgg tttttctgcc accg                                          24

<210> SEQ ID NO 3
<211> LENGTH: 24
<212> TYPE: DNA
<213> ORGANISM: Artificial Sequence
<220> FEATURE:
<223> OTHER INFORMATION: chemically synthesized primer

<400> SEQUENCE: 3
actgcccctc atcagactgc tact                                          24

<210> SEQ ID NO 4
<211> LENGTH: 24
<212> TYPE: DNA
<213> ORGANISM: Artificial Sequence
<220> FEATURE:
<223> OTHER INFORMATION: chemically synthesized primer

<400> SEQUENCE: 4
cactgccttg tactcgggta gctg                                          24

<210> SEQ ID NO 5
<211> LENGTH: 24
<212> TYPE: DNA
<213> ORGANISM: Artificial Sequence
<220> FEATURE:
<223> OTHER INFORMATION: chemically synthesized primer

<400> SEQUENCE: 5
acgagtggca gtttcttctt ggga                                          24

<210> SEQ ID NO 6
<211> LENGTH: 24
<212> TYPE: DNA
<213> ORGANISM: Artificial Sequence
<220> FEATURE:
<223> OTHER INFORMATION: chemically synthesized primer

<400> SEQUENCE: 6
tatgactcac ttccaggggg cact                                          24

<210> SEQ ID NO 7
<211> LENGTH: 23
<212> TYPE: DNA

```
<213> ORGANISM: Artificial Sequence
<220> FEATURE:
<223> OTHER INFORMATION: chemically synthesized primer

<400> SEQUENCE: 7
tctttccacc aggcccccgg ctc                                              23

<210> SEQ ID NO 8
<211> LENGTH: 23
<212> TYPE: DNA
<213> ORGANISM: Artificial Sequence
<220> FEATURE:
<223> OTHER INFORMATION: chemically synthesized primer

<400> SEQUENCE: 8
tgcgggcgga catggggaga tcc                                              23

<210> SEQ ID NO 9
<211> LENGTH: 23
<212> TYPE: DNA
<213> ORGANISM: Artificial Sequence
<220> FEATURE:
<223> OTHER INFORMATION: chemically synthesized primer

<400> SEQUENCE: 9
tagagctaga ctccgggcga tga                                              23

<210> SEQ ID NO 10
<211> LENGTH: 23
<212> TYPE: DNA
<213> ORGANISM: Artificial Sequence
<220> FEATURE:
<223> OTHER INFORMATION: chemically synthesized primer

<400> SEQUENCE: 10
ttgccttaaa caagaccacg aaa                                              23

<210> SEQ ID NO 11
<211> LENGTH: 24
<212> TYPE: DNA
<213> ORGANISM: Artificial Sequence
<220> FEATURE:
<223> OTHER INFORMATION: chemically synthesized primer

<400> SEQUENCE: 11
gcgaactcac acaggcgaga aacc                                             24

<210> SEQ ID NO 12
<211> LENGTH: 23
<212> TYPE: DNA
<213> ORGANISM: Artificial Sequence
<220> FEATURE:
<223> OTHER INFORMATION: chemically synthesized primer

<400> SEQUENCE: 12
tcgcttcctc ttcctccgac aca                                              23

<210> SEQ ID NO 13
<211> LENGTH: 28
<212> TYPE: DNA
<213> ORGANISM: Artificial Sequence
<220> FEATURE:
<223> OTHER INFORMATION: chemically synthesized primer

<400> SEQUENCE: 13
tgacctaact cgaggaggag ctggaatc                                         28
```

```
<210> SEQ ID NO 14
<211> LENGTH: 32
<212> TYPE: DNA
<213> ORGANISM: Artificial Sequence
<220> FEATURE:
<223> OTHER INFORMATION: chemically synthesized primer

<400> SEQUENCE: 14
aagtttgagg cagttaaaat tatggctgaa gc                                    32

<210> SEQ ID NO 15
<211> LENGTH: 20
<212> TYPE: DNA
<213> ORGANISM: Artificial Sequence
<220> FEATURE:
<223> OTHER INFORMATION: chemically synthesized primer

<400> SEQUENCE: 15
caccatggag aaggccgggg                                                  20

<210> SEQ ID NO 16
<211> LENGTH: 20
<212> TYPE: DNA
<213> ORGANISM: Artificial Sequence
<220> FEATURE:
<223> OTHER INFORMATION: chemically synthesized primer

<400> SEQUENCE: 16
gacggacaca ttgggggtag                                                  20

<210> SEQ ID NO 17
<211> LENGTH: 24
<212> TYPE: DNA
<213> ORGANISM: Artificial Sequence
<220> FEATURE:
<223> OTHER INFORMATION: chemically synthesized primer

<400> SEQUENCE: 17
ggttttttag aggatggttg agtg                                             24

<210> SEQ ID NO 18
<211> LENGTH: 23
<212> TYPE: DNA
<213> ORGANISM: Artificial Sequence
<220> FEATURE:
<223> OTHER INFORMATION: chemically synthesized primer

<400> SEQUENCE: 18
tccaacccta ctaacccatc acc                                              23

<210> SEQ ID NO 19
<211> LENGTH: 30
<212> TYPE: DNA
<213> ORGANISM: Artificial Sequence
<220> FEATURE:
<223> OTHER INFORMATION: chemically synthesized primer

<400> SEQUENCE: 19
gattttgtag gtgggattaa ttgtgaattt                                       30

<210> SEQ ID NO 20
<211> LENGTH: 30
<212> TYPE: DNA
<213> ORGANISM: Artificial Sequence
<220> FEATURE:
<223> OTHER INFORMATION: chemically synthesized primer
```

```
<400> SEQUENCE: 20
accaaaaaaa cccacactca tatcaatata                                30

<210> SEQ ID NO 21
<211> LENGTH: 25
<212> TYPE: DNA
<213> ORGANISM: Artificial Sequence
<220> FEATURE:
<223> OTHER INFORMATION: chemically synthesized primer

<400> SEQUENCE: 21
cagccccgat tcttccacca gtccc                                     25

<210> SEQ ID NO 22
<211> LENGTH: 25
<212> TYPE: DNA
<213> ORGANISM: Artificial Sequence
<220> FEATURE:
<223> OTHER INFORMATION: chemically synthesized primer

<400> SEQUENCE: 22
cggaagattc ccagtcgggt tcacc                                     25

<210> SEQ ID NO 23
<211> LENGTH: 24
<212> TYPE: DNA
<213> ORGANISM: Artificial Sequence
<220> FEATURE:
<223> OTHER INFORMATION: chemically synthesized primer

<400> SEQUENCE: 23
gacaggggga ggggaggagc tagg                                      24

<210> SEQ ID NO 24
<211> LENGTH: 26
<212> TYPE: DNA
<213> ORGANISM: Artificial Sequence
<220> FEATURE:
<223> OTHER INFORMATION: chemically synthesized primer

<400> SEQUENCE: 24
cttccctcca accagttgcc ccaaac                                    26

<210> SEQ ID NO 25
<211> LENGTH: 26
<212> TYPE: DNA
<213> ORGANISM: Artificial Sequence
<220> FEATURE:
<223> OTHER INFORMATION: chemically synthesized primer

<400> SEQUENCE: 25
gggaaatggg aggggtgcaa aagagg                                    26

<210> SEQ ID NO 26
<211> LENGTH: 26
<212> TYPE: DNA
<213> ORGANISM: Artificial Sequence
<220> FEATURE:
<223> OTHER INFORMATION: chemically synthesized primer

<400> SEQUENCE: 26
ttgcgtgagt gtggatggga ttggtg                                    26

<210> SEQ ID NO 27
<211> LENGTH: 24
<212> TYPE: DNA
```

```
<213> ORGANISM: Artificial Sequence
<220> FEATURE:
<223> OTHER INFORMATION: chemically synthesized primer

<400> SEQUENCE: 27
cagatcctaa acagctcgca gaat                                          24

<210> SEQ ID NO 28
<211> LENGTH: 23
<212> TYPE: DNA
<213> ORGANISM: Artificial Sequence
<220> FEATURE:
<223> OTHER INFORMATION: chemically synthesized primer

<400> SEQUENCE: 28
gcgtacgcaa attaaagtcc aga                                           23

<210> SEQ ID NO 29
<211> LENGTH: 20
<212> TYPE: DNA
<213> ORGANISM: Artificial Sequence
<220> FEATURE:
<223> OTHER INFORMATION: chemically synthesized primer

<400> SEQUENCE: 29
gtcaaggccg agaatgggaa                                               20

<210> SEQ ID NO 30
<211> LENGTH: 20
<212> TYPE: DNA
<213> ORGANISM: Artificial Sequence
<220> FEATURE:
<223> OTHER INFORMATION: chemically synthesized primer

<400> SEQUENCE: 30
gcttcaccac cttcttgatg                                               20
```

METHOD FOR EFFICIENT PRODUCTION OF INDUCED PLURIPOTENT STEM CELLS UTILIZING CELLS DERIVED FROM ORAL MUCOSA

TECHNICAL FIELD

The present invention relates to a method for producing induced pluripotent stem cells with high establishment efficiency. More specifically, the present invention relates to a method for producing induced pluripotent stem cells with high establishment efficiency by utilizing oral mucosa-derived somatic cells. Further, the present invention relates to induced pluripotent stem cells produced by the above production method.

BACKGROUND ART

In order to promote recovery of the morphology and function of living tissue removed by tumorectomy and the like, there is a desire for the development of a new treatment method based on cell transplantation, in addition to the conventional replacement techniques that use biomaterials. In recent years, with regard to bone tissue and the like, regenerative therapies that use tissue stem cells such as bone marrow-derived mesenchymal stem cells are approaching the practical stage (see NPL 1). However, bone marrow puncture is necessary to obtain bone marrow-derived mesenchymal stem cells, and it is difficult to acquire the number of stem cells necessary for the treatment. Therefore, there is a desire for a source of stem cells that can be more safely and easily.

At the same time, in recent years, a technique to reprogram the somatic cells and induce them into pluripotent stem (iPS) cells, in which genes respectively encoding OCT3/4, KLF4, c-MYC, and SOX2 are introduced into somatic cells was reported, and innovative techniques have been provided in the field of regenerative medicine (see NPL 1). The progress in iPS cell research is remarkable, and the application thereof in regenerative medicine is drawing attention as a national project.

iPS cells can be produced from the patient's own somatic cells; are free from immunological rejection; and raise fewer ethical issues. Therefore, iPS cells are expected to be put into practical use for clinical purposes. Conventionally, dermal fibroblasts have been primarily used to produce iPS cells. However, it has been reported that iPS cells can also be produced from liver and stomach cells (see NPL 2), peripheral blood (see NPL 3), and extracted wisdom teeth cells. Nevertheless, the conventional somatic cells used for producing iPS cells face the following problems: iPS cell establishment efficiency is low; and such cells do not provide a stable supply source of iPS cells. Further, the conventional somatic cells used for producing iPS cells are also disadvantageous in terms of the burden on the patient, because collection of the somatic cells accompanies surgical invasion of living organisms.

With a background based on such conventional techniques, there is a keen desire for the development of a technique for producing iPS cells with less burden on the patient, and high establishment efficiency.

CITATION LIST

Patent Literature

PTL 1: WO 2007/069666

Non-Patent Literature

NPL 1: Yamada Y, et al. Injectable tissue-engineered bone using autogenous bone marrow-derived stromal cells for maxillary sinus augmentation: Clinical application report from a 2-6-year follow-up. Tissue Eng Part A 2008; 14: 1699-707.

NPL 2: Aoi T et al. Passage of pluripotent stem cells from adult mouse liver and stomach cells. Science 2008; 321: 699-702.

NPL 3: Loh Y H et al. Passage of induced pluripotent stem cells from human blood. Blood 2009; in press.

SUMMARY OF INVENTION

Technical Problem

An object of the present invention is to provide a technique to produce iPS cells with less burden on the patient and with high establishment efficiency.

Solution to Problem

The present inventors conducted extensive studies to accomplish the above object. As a result, they found that iPS cells can be efficiently produced with significantly improved establishment efficiency by selecting from among various somatic cells, cells derived from oral mucosa, which can be collected with less burden on the patient; and introducing, into the cells, reprogramming factors capable of inducing the cells into pluripotent stem cells. The present invention was completed by further studies based on the above findings.

Specifically, the present invention provides the following embodiments.

Item 1. A method for producing induced pluripotent stem cells, comprising a step of introducing reprogramming factors capable of inducing somatic cells into pluripotent stem cells, into oral mucosa-derived somatic cells.

Item 2. The production method according to Item 1, wherein the oral mucosa-derived somatic cells are oral mucosal fibroblasts.

Item 3. The production method according to Item 1, wherein the oral mucosa-derived somatic cells are gingival fibroblasts.

Item 4. The production method according to Item 1, wherein the reprogramming factors capable of inducing somatic cells into pluripotent stem cells comprise an Oct family gene, a Sox family gene, and a Klf family gene.

Item 5. The production method according to Item 4, wherein the reprogramming factors capable of inducing somatic cells into pluripotent stem cells further comprise a Myc family gene.

Item 6. Induced pluripotent stem cells obtained by introducing reprogramming factors capable of inducing somatic cells into pluripotent stem cells, into oral mucosa-derived somatic cells.

Item 7. The induced pluripotent stem cells according to Item 6, wherein the oral mucosa-derived somatic cells are oral mucosal fibroblasts.

Item 8. The induced pluripotent stem cells according to Item 6, wherein the oral mucosa-derived somatic cells are gingival fibroblasts.

Item 9. The induced pluripotent stem cells according to Item 6, wherein the reprogramming factors capable of inducing cells into pluripotent stem cells comprise an Oct family gene, a Sox family gene, and a Klf family gene.

Item 10. The induced pluripotent stem cells according to Item 9, wherein the reprogramming factors capable of inducing somatic cells into pluripotent stem cells further comprise a Myc family gene.

Item 11. A cell preparation for use in regenerative medicine, the cell preparation comprising the induced pluripotent stem cells according to any one of Items 6 to 10.

Advantageous Effects of Invention

According to the present invention, the use of oral mucosa-derived somatic cells for induction of iPS cells allows the iPS cell establishment efficiency to be improved and iPS cells to be established in a shorter period of time than before.

To collect cells from oral mucosa, it is possible to use gingival tissue to be discarded during gingivectomy and the like in general dental treatments such as tooth extraction, periodontal treatment, and implant treatment. The technique to establish iPS cells using tissue to be discarded during a course of treatment is expected to contribute to tissue regenerative medicine that is keenly desired in the medical and dental fields. In addition, such a technique facilitates banking of iPS cells that can be established in a less invasive manner, allows one's own iPS cells to be easily used for future illness, and can contribute to the development of regenerative medicine in various fields.

Further, in the present invention, when oral mucosa fibroblasts (particularly gingival fibroblasts of oral mucosa) are used as oral mucosa-derived somatic cells, the cells can be induced into iPS cells with high establishment efficiency, even after the fibroblasts are repeatedly subcultured. Therefore, the use of oral mucosal fibroblasts is preferable particularly in clinical application, as a source of cells to be induced into iPS cells.

BRIEF DESCRIPTION OF DRAWINGS

FIG. 4 also shows the results obtained by crystal violet staining the cells 9 days after transduction with four factors (c-Myc, Oct3/4, Sox, and Klf4).

In FIG. 12, the black circles indicate methylated CpG sites, and white circles indicate unmethylated CpG sites.

FIG. 15A shows the results obtained by measuring the iPS cell establishment efficiency when four factors (c-Myc, Oct3/4, Sox, and Klf4) were introduced into mouse gingival fibroblasts and mouse tail-tip fibroblasts cultured for 4 passages (P4), 7 passages (P7), and 10 passages (P10). FIG. 15B shows the results obtained by measuring the growth characteristics of the mouse gingival fibroblasts and mouse tail-tip fibroblasts cultured for 5 passages. FIG. 15C shows the results obtained by measuring, by real-time RT-PCR, the endogenous expression of Tert required for maintenance of telomere that contributes to cell proliferation, in mouse gingival fibroblasts and mouse tail-tip fibroblasts cultured for 4 passages (P4), 5 passages (P5), and 6 passages (P6).

FIG. 16A shows an image obtained when human gingival tissue fragments for the test were collected. FIG. 16B shows the results obtained by observing human gingival fibroblasts and human gingival epithelial cells, which were grown from the human gingival tissue fragments. FIG. 16C shows the results obtained by observing human gingival fibroblasts used for induction into iPS cells. FIG. 16D shows the results obtained by observing iPS cells induced by introducing four factors (c-Myc, Oct3/4, Sox, and Klf4) into human gingival fibroblasts. FIGS. 16E and 16F show the results obtained by observing cloned iPS cells induced by introducing four factors (c-Myc, Oct3/4, Sox, and Klf4) into human gingival fibroblasts. FIG. 16G shows the results obtained by observing human ES cells. FIG. 16H shows the results obtained by observing iPS cells induced from human dermal fibroblasts. FIG. 16I shows the results obtained by alkaline phosphatase staining, iPS cells induced by introducing four factors (c-Myc, Oct3/4, Sox, and Klf4) into human gingival fibroblasts.

DESCRIPTION OF EMBODIMENTS

Figure 1:
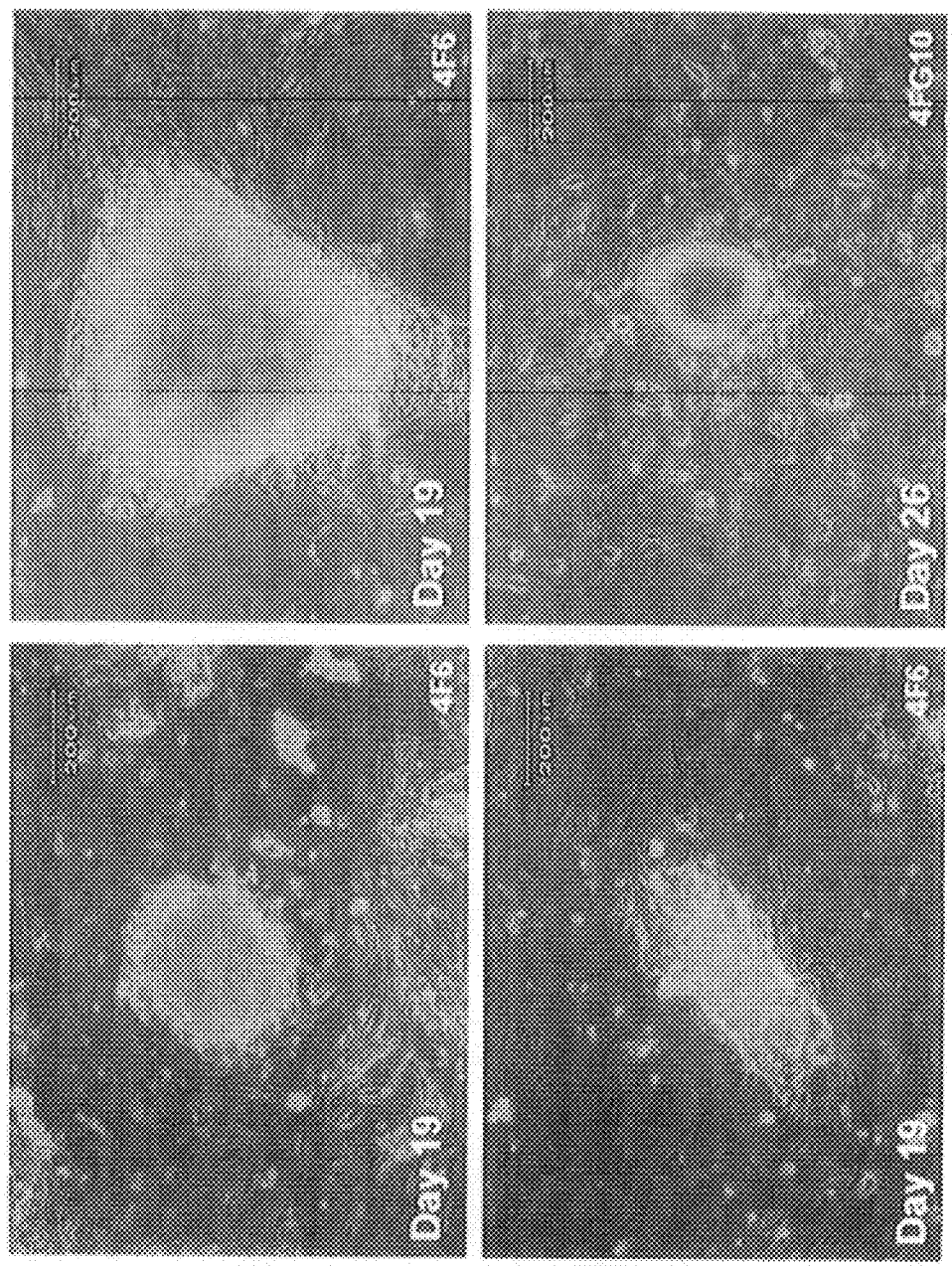
FIG. 1 shows the results obtained in Example 1 by observing the cell morphology of mouse gingival fibroblasts 19 to 26 days after transduction with four factors (c-Myc, Oct3/4, Sox, and Klf4) (the cells here are seeded onto feeder cells).

The method of the present invention for producing iPS cells is characterized by comprising a step of introducing, into oral mucosa-derived somatic cells, reprogramming factors capable of inducing somatic cells into pluripotent stem cells. The present invention is described in detail below.

In the present invention, iPS cells are induced from oral mucosa-derived somatic cells. Somatic cells used in the present invention are oral mucosa-derived somatic, and gingival cells are preferably used in order to induce iPS cells with high establishment efficiency. Oral mucosa-derived somatic cells used in the present invention may be either fibroblasts or epithelial cells of oral mucosa, with gingival fibroblasts and gingival epithelial cells being preferable, and gingival fibroblasts being further preferable. Oral mucosa fibroblasts, particularly gingival fibroblasts, can be induced into iPS cells with high establishment efficiency, and the iPS cell establishment efficiency can be maintained even after the cells are subcultured. It is conventionally known that somatic cells used to be induced into iPS cells exhibit a decrease in the establishment efficiency after subculture. However, in the case of oral mucosa fibroblasts, they can be induced into iPS cells with high establishment efficiency even after they were cultured for, for example, about 7 to 10 passages. Oral mucosa fibroblasts are excellent in convenience for use, and the clinical usefulness thereof is considered to be extremely high.

Further, the oral mucosa-derived somatic cells are suitably selected from somatic cells from mammals such as humans, mice, rats, hamsters, rabbits, cats, dogs, sheep, pigs, bovines, goats, monkeys, and the like according to the intended purpose of iPS cells that are induced. When the somatic cells are used for the purpose of treating humans and providing tools for development of drugs to treat humans, it is preferable to use human somatic cells. Still further, when somatic cells derived from human oral mucosa are used, somatic cells derived from any of fetuses, infants, children, and adults may be used. When iPS cells to be induced are used for the purpose of treating humans, it is preferable to use oral mucosa-derived somatic cells collected from the patient. As the oral mucosa-derived somatic cells to be used, it is also possible to use gingival tissue to be discarded during gingivectomy or the like in tooth extraction, periodontal treatment, implant treatment, or the like. Cells from oral mucosa are collected, for example, according to a method reported by Nikawa et al. (Nikawa H, Egusa H, Makihira S, Okamoto T, Kurihara H, Shiba H, Amano H, Murayama T, Yatani H, Hamada T, "An in vitro evaluation of the adhesion of Candida species to oral and lung tissue cells," Mycoses, 2006; 49 (1):14-7). Specifically, cells can be collected from oral mucosa by the following method: collected oral mucosal tissue is closely attached to a tissue culture plate, allowed to stand, and cultured at 37° C. with 5% $CO_2$, and cells thereby grown from the tissue are collected.

Reprogramming factors for inducing oral mucosa-derived somatic cells into iPS cells are not particularly limited, insofar as they can induce somatic cells into pluripotent stem cells. Generally, examples thereof include a combination of three factors comprising (1) an Oct family gene or its gene product, (2) a Sox family gene or its gene product, and (3) a klf family gene or its gene product. Further, from the viewpoint of further improving iPS cell establishment efficiency, it is preferable to combine (4) a Myc family gene or its gene product, in addition to the three factors described above. Further, in the induction of reprogramming of cells, the use of low-molecular compounds such as DNA methyltransferase inhibitors (5-Azacytidine and 5-Aza-2'-deoxycytidine) and histone deacetylase inhibitors (valproic acid, trichostatin A, suberoylanilide hydroxamic acid, and the like) makes it possible to improve the iPS cell induction efficiency by the reprogramming factors, and a combination of low-molecular compounds can be used by itself as a reprogramming factor.

Examples of Oct families include Oct3/4, Oct1A, Oct 6, and the like. These Oct families may be used singly, or in a combination of two or more thereof. Of these OCT families, Oct3/4 is preferably used from the viewpoint of efficient induction into the iPS cells. The base sequence of Oct3/4 is known (NCBI accession Number NM_002701 (human), NM_013633 (Mouse)). Further, the base sequence of Oct1A (NCBI accession Number NM_002697 (human), NM_198934 (Mouse)) and the base sequence of Oct6 (NCBI accession Number NM_002699 (human), NM_011141 (Mouse)) are also known.

Examples of Sox families include Sox1, Sox2, Sox3, Sox7, Sox15, Sox17, and Sox18. These Sox families may be used singly, or in a combination of two or more thereof. Of these Sox families, Sox2 is preferably used from the viewpoint of efficient induction into iPS cells. The base sequence of Sox2 is known (NCBI accession Number NM_003106 (human), NM_011443 (Mouse)). Further, the base sequence of Sox1 (NCBI accession Number NM_005986 (human), NM_009233 (Mouse)), the base sequence of Sox3 (NCBI accession Number NM_005634 (human), NM_009237 (Mouse)), the base sequence of Sox7 (NCBI accession Number NM_031439 (human), NM_011446 (Mouse)), the base sequence of Sox15 (NCBI accession Number NM_006942 (human), NM_009235 (Mouse)), the base sequence of Sox17 (NCBI accession Number NM_0022454 (human), NM_011441 (Mouse)), and the base sequence of Sox18 (NCBI accession Number NM_018419 (human), NM_009236 (Mouse)) are also known.

Examples of Klf families include Klf1, Klf2, Klf4, Klf5, and the like. These Klf families may be used singly, or in a combination of two or more thereof. Of these Klf families, Klf4 is preferably used from the viewpoint of efficient induction into iPS cells. The base sequence of Klf4 is known (NCBI accession number NM_010637 (human), NM_004235 (Mouse)). Further, the base sequence of Klf1 (NCBI accession number NM_006563 (human), NM 010635 (Mouse)), the base sequence of Klf2 (NCBI accession number NM_016270 (human), NM_008452 (Mouse)), and the base sequence of Klf5 (NCBI accession number NM_001730 (human), NM 009769 (Mouse)) are also known.

Examples of Myc families include c-Myc, N-Myc, L-Myc, and the like. These Myc families may be used singly, or in a combination of two or more thereof. Of these Myc families, c-Myc and L-Myc are preferably used, and c-Myc is further preferably used in the present invention. c-Myc is known as a transcriptional regulator that is involved in cell differentiation and growth (S. Adhikary, M. Elilers, Nat. Ray. Mol. Cell. Biol., 6, pp. 635-645, 2005), and the base sequence thereof is known (NCBI accession number NM_010849 (human), NM 002467 (Mouse)). Further, the base sequence of N-Myc (NCBI accession number NM_005378 (human), NM_008709 (Mouse)) and the base sequence of L-Myc (NCBI accession number NM_005376 (human), NM 008506 (Mouse)) are also known. The term "NCBI" used in the specification is an abbreviation for National Center for Biotechnology Information of the United States of America.

The reprogramming factors described above are commonly present in mammals including humans, and reprogramming factors derived from any mammal can be used. However, it is preferable to suitably select the factors according to the origin of somatic cells into which the factors are introduced. For example, when human somatic cells are used, the reprogramming factors described above are preferably derived from humans. Further, the reprogramming factors may also comprise, in addition to a wild-type gene or its gene product, a mutated gene product in which several amino acids (for example, 1 to 10, preferably 1 to 6, further preferably 1 to 4, still further preferably 1 to 3, particularly preferably 1 or 2 amino acids) in the amino acid sequence of the gene product are substituted, deleted, and/or inserted, and in which the gene product has a function equivalent to that of a wild-type gene product; or a mutated gene encoding such a mutated gene product.

In the present invention, the reprogramming factors can be prepared according to a common method, based on known sequence information. For example, cDNA of a desired gene can be prepared by extracting RNA from mammalian cells, and cloning the RNA according to a common method.

Either genes (nucleic acid molecules) or gene products (proteins) may be used as the reprogramming factors to be introduced into oral mucosa-derived somatic cells, insofar as they are capable of inducing somatic cells into pluripotent stem cells. However, genes (nucleic acid molecules) are preferable from the viewpoint of improving the iPS cell establishment efficiency.

The reprogramming factors can be introduced into oral mucosa-derived somatic cells according to a known method. For example, when the reprogramming factors are genes, the reprogramming factors can be introduced into oral mucosa-derived somatic cells by a method commonly used for transfection of animal cells. Specific examples of methods for introducing the reprogramming factor into somatic cells include a method that uses a vector; calcium phosphate method; lipofection; electroporation; microinjection method; and the like. Of these, a method that uses a vector is preferable in terms of induction efficiency. When the reprogramming factors are introduced into somatic cells using a vector, vectors such as viral vectors, nonviral vectors, and artificial viruses can be used. Viral vectors such as adenoviruses and retroviruses can be preferably used in terms of safety. When a vector is used, the reprogramming factors may be introduced in such a manner that each gene is incorporated into separate vectors, or that two or more genes are incorporated into one vector. Further, when the reprogramming factors are introduced into somatic cells using a vector, it is also possible to use a protein expression vector in which the coding sequences of the reprogramming factors are linked to the coding sequence of 2A peptide.

In the present invention, the reprogramming factors used to induce oral mucosa-derived somatic cells into iPS cells are not limited to the above-described examples or nucleic acids, but encompass conventionally known reprogramming factors and new reprogramming factors that will be developed in the future.

The oral mucosa-derived somatic cells transduced with the reprogramming factors are reprogrammed herein, and results in the attainment of self-renewal and pluripotency. Thus, the somatic cells are induced into undifferentiated cells with pluripotency and self-renewal (iPS cells). Oral mucosa-derived somatic cells transduced with the reprogramming factors are induced into iPS cells by being cultured for about 9 to 15 days. The present invention is advantageous in that the period in which cells are induced into iPS cells after transduction with the reprogramming factors is short compared to conventional techniques, and in that iPS cells can be established in a short period of time.

iPS cells can be selected from oral mucosa-derived somatic cells transduced with the reprogramming factors, by using, as indicators, the presence or absence of proliferation potential of the cells, properties specific to iPS cells, and the like. Specifically, iPS cells can be selected from the cells having proliferation potential by using, as indicators, the cellular form and the presence or absence of maker genes (such as Nanog, Eras, Zfp42, and endogenous Oct3/4) specific to iPS cells, stainability of alkaline phosphatase, and ability to form teratomas in the body of mice.

The thus-obtained iPS cells have, in addition to the self-renewal, a potential to differentiate into various cells such as nerve cells, hepatic cells, smooth muscle cells, osteoblasts, and myocardial cells; and can renew various tissues such as epidermal tissue, muscle tissue, fat tissue, nerve tissue, cartilage tissue, bone tissue, and gut-like epithelial tissue. Therefore, such cells can be used for various purposes in regenerative medicine. Specifically, the thus-obtained iPS cells can be used as a cell preparation for regenerative medicine. Further, the thus-obtained iPS cells can also be used as a tool for developing drugs, by evaluating the responsiveness of the cells to various drugs.

EXAMPLES

The present invention is described in detail below with reference to Examples and the like; however, the present invention is not limited thereto.

Example 1

Preparation and Evaluation of Mouse iPS Cells iPS cells were induced from mouse gingival fibroblasts or tail-tip fibroblasts with the experimental materials and conditions described below, and the properties of the induced iPS cells were evaluated.

<Isolation and Culture of Mouse Gingival Fibroblasts and Tail-Tip Fibroblasts>

Oral mucosa gingival tissue and tail tissue were collected from male 10-week-old C57BL/6J mice. These tissue fragments were closely attached to 0.1% gelatin-coated tissue culture plates, and allowed to stand at 37° C. with 5% $CO_2$, with MF-start medium (Toyobo, Osaka) added to the plates to an amount that cover the tissue fragments. When fibroblasts were thoroughly grown from the tissue fragments, these tissue fragments were removed, thereby obtaining fibroblasts. The culture medium was replaced with fresh culture medium every 2 to 3 days. Cells were subcultured when they were 70% confluent, and the culture medium was replaced with FP medium (DMEM (Dulbecco's modified Eagle medium without sodium pyruvate: Nacalai Tesque, Kyoto) medium containing 10% fetal bovine serum (Sigma, St. Louis, Mo.), 50 units/ml penicillin, and 50 μg/ml streptomycin)) to continue culturing.

<Mouse Embryo-Stem (ES) Cell Line and Feeder Cells>

Mouse embryo-stem (ES) cell line (AB2.2) and SNLP76.7-4 feeder cells supplied by Dr. Allan Bradley (Sanger Institute, London, UK) were used.

<Production of Retrovirus Particles>

Retroviral vectors (pMXs-IRES-puro) containing mouse c-Myc, Oct3/4, Sox2, or Klf4 (cDNA) were purchased from Addgene (Cambridge, Mass.). Additionally, a retroviral vector (pMX-GFP) containing green fluorescent protein (GFP) gene purchased from Cell Biolabs (San Diego, Calif.) was used in order to confirm the transduction efficiency of the retroviral vectors. Platinum-E packaging cells supplied by Dr. Toshio Kitamura (University of Tokyo, Japan) were used to produce virus particles.

Each plasmid vector (9 μg) was mixed with a mixture solution of OPTI-MEMI medium (Invitrogen) and FuGENE 6 reagent (Roche, Basel, Switzerland), and the mixture was transfected into Platinum-E cells by the lipofection method. The culture supernatant containing each virus particle was collected 24 hours after transfection, and used for retroviral infection (iPS cell induction) of gingival fibroblasts or tail-tip fibroblasts.

<Induction of iPS Cells>

Twenty-four hours before transduction by retroviral infection, $5 \times 10^5$ gingival fibroblasts cultured for 4 to 10 passages were seeded into 0.1% gelatin-coated 10-cm culture plates, and cultured in FP medium containing bFGF (final concentration of 3 ng/m: PeproTech, London, UK). Induction of iPS cells was performed using four factors (c-Myc, Oct3/4, Sox, and Klf4), or three factors (Oct3/4, Sox, and Klf4) without c-Myc. For iPS cell induction, the supernatant containing each virus of the four or three factors was mixed in such a manner that the factors would ultimately be present in equal amounts. When GFP was used, c-Myc, Oct3/4, Sox, Klf4, and GFP were mixed at a ratio of 1:1:1:1:3; and Oct3/4, Sox, Klf4, and GFP were mixed at a ratio of 1:1:1:3. Each fibroblast culture medium was replaced with a solution in which polybrene (final concentration: 4 μg/ml) and bFGF (final concentration: 10 ng/ml) were added to the above mixture, and the cells were cultured overnight at 37° C. with 5% $CO_2$. On the next day and two days after that, the culture supernatant was removed by suction and replaced with FP medium containing bFGF (final concentration: 3 ng/ml). Four days after transduction, transduced fibroblasts were seeded onto mitomycin C-inactivated SNLP76.7-4 feeder cells ($2.6 \times 10^4$ cells/cm$^2$). In regard to the concentration of seeded cells, $0.1 \times 10^3$ to $1 \times 10^3$ cells/cm$^2$ were used for induction using the four factors, and $0.7 \times 10^4$ to $1 \times 10^4$ cells/cm$^2$ were used for induction using the three factors. On the following day, the culture medium was replaced with ES medium (DMEM medium containing 15% bovine serum, 2 mM L-Glutamine, $1 \times 10^{-4}$ M nonessential amino acids, $1 \times 10^{-4}$ M 2-mercaptoethanol, 50 U penicillin, and 50 μg/ml streptomycin). Thereafter, the culture medium was replaced daily with fresh medium. Several colonies exhibiting ES cell-like morphology, which emerged after transduction (9 to 21 days after transduction in the case of induction with the four factors; and 35 to 50 days after transduction in the case of induction with the three factors), were selected and subcultured. Among the colonies that were cloned, cell lines derived from colonies of cells particularly exhibiting ES cell-like morphology and proliferation potential were regarded as iPS cell lines.

Figure 2:
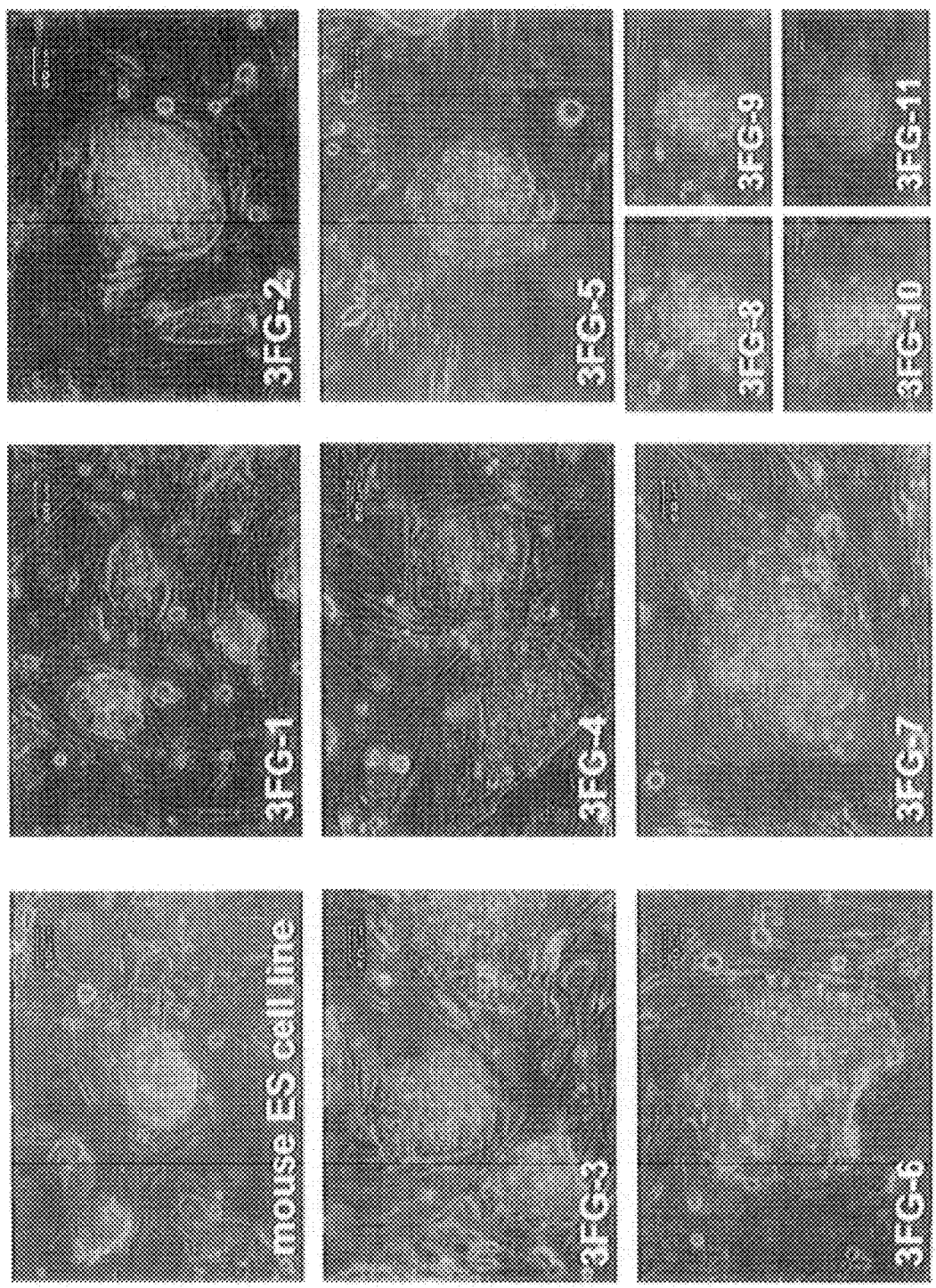
FIG. 2 shows the results obtained in Example 1 by observing the cell morphology of cloned 11 iPS cell lines which were obtained by introducing three factors (Oct3/4, Sox, and Klf4) into mouse gingival fibroblasts; and the cell morphology of mouse ES cells (the cells here are seeded onto feeder cells).

FIGS. 1 and 2 show the results obtained by observing cells when iPS cells were induced by introducing the four or three factors into gingival fibroblasts cultured for 6 passages. FIG. 1 shows the results obtained by observing cells seeded onto feeder cells (19 to 26 days after transduction in the case of introduction of the four factors). FIG. 2 shows induced on feeder cells for 35 to 50 days after transduction with the three factors (gingival fibroblasts after 6 passages were used for induction); and mouse ES cells. These results clearly show that the cells obtained by introducing the four or three factors into gingival fibroblasts exhibit ES cell-like morphology and were induced into iPS cells.

Figure 3:
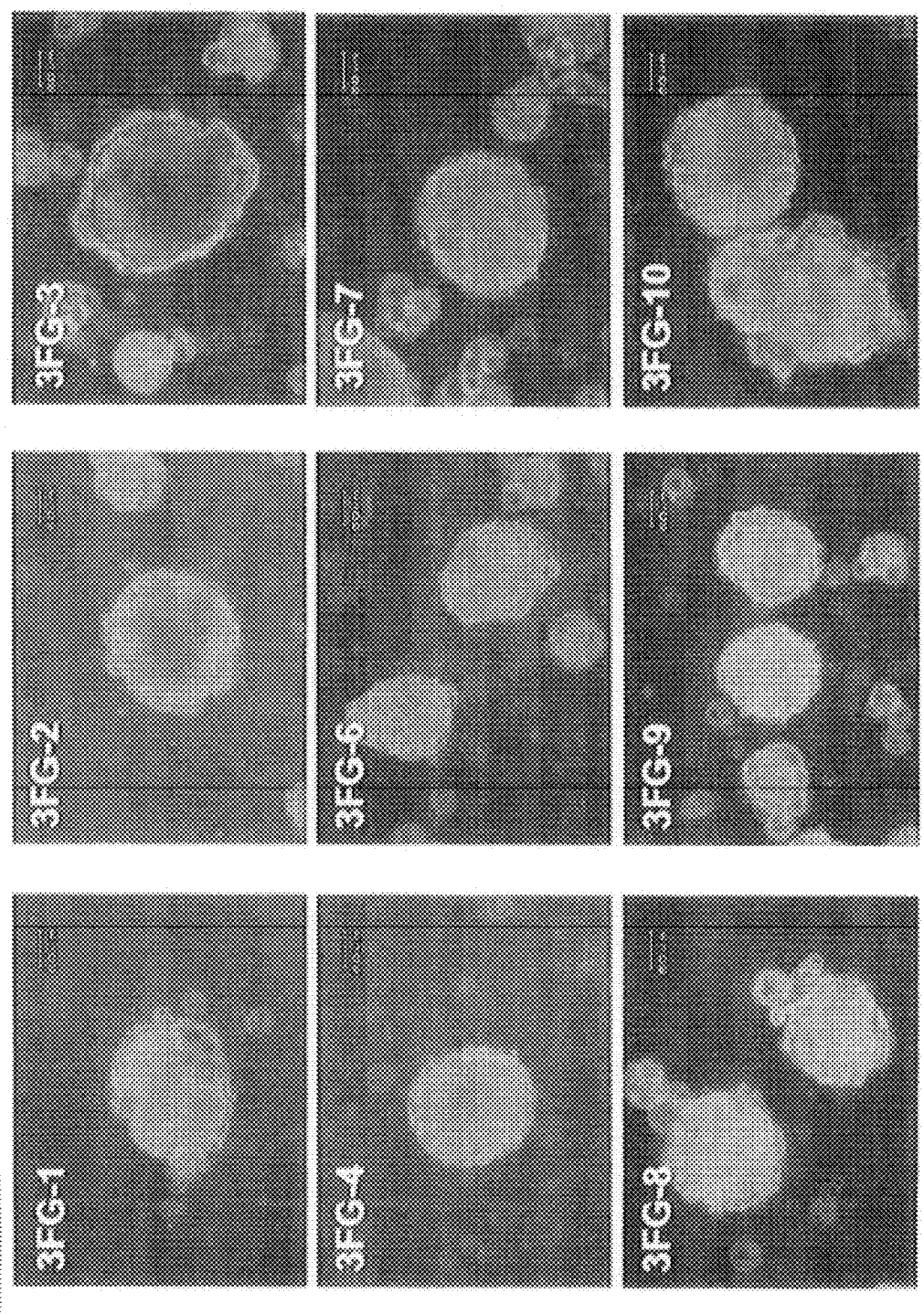
FIG. 3 shows the results obtained in Example 1 by observing the cell morphology of iPS cell clone lines prepared by introducing three factors (Oct3/4, Sox, and Klf4) into mouse gingival fibroblasts, and cultured free-floating in ES medium for 3 days.

Further, 9 iPS cell lines induced by introducing the three factors into gingival fibroblasts cultured for 6 passages were cultured free-floating in ES medium for 3 days, and the cell morphology (formation of embryoid bodies) was observed. FIG. 3 shows the results.

<Comparison of iPS Cell Establishment Efficiency Between Gingival Fibroblasts and Tail-Tip Fibroblasts>

Gingival fibroblasts and tail-tip fibroblasts were simultaneously isolated from the gingiva and tail of the same male 10-week-old mouse, and cultured. These cells were concurrently cultured for 6 passages. These cells were seeded into 6-well culture plates at a concentration of $1 \times 10^4$ to $2 \times 10^4$ cells/well, and iPS cells induction using the above four factors were performed under the same conditions. Cell colonies that emerged after transduction were detected by crystal violet staining, and the numbers of ES cell-like colonies were compared and examined.

Figure 4:
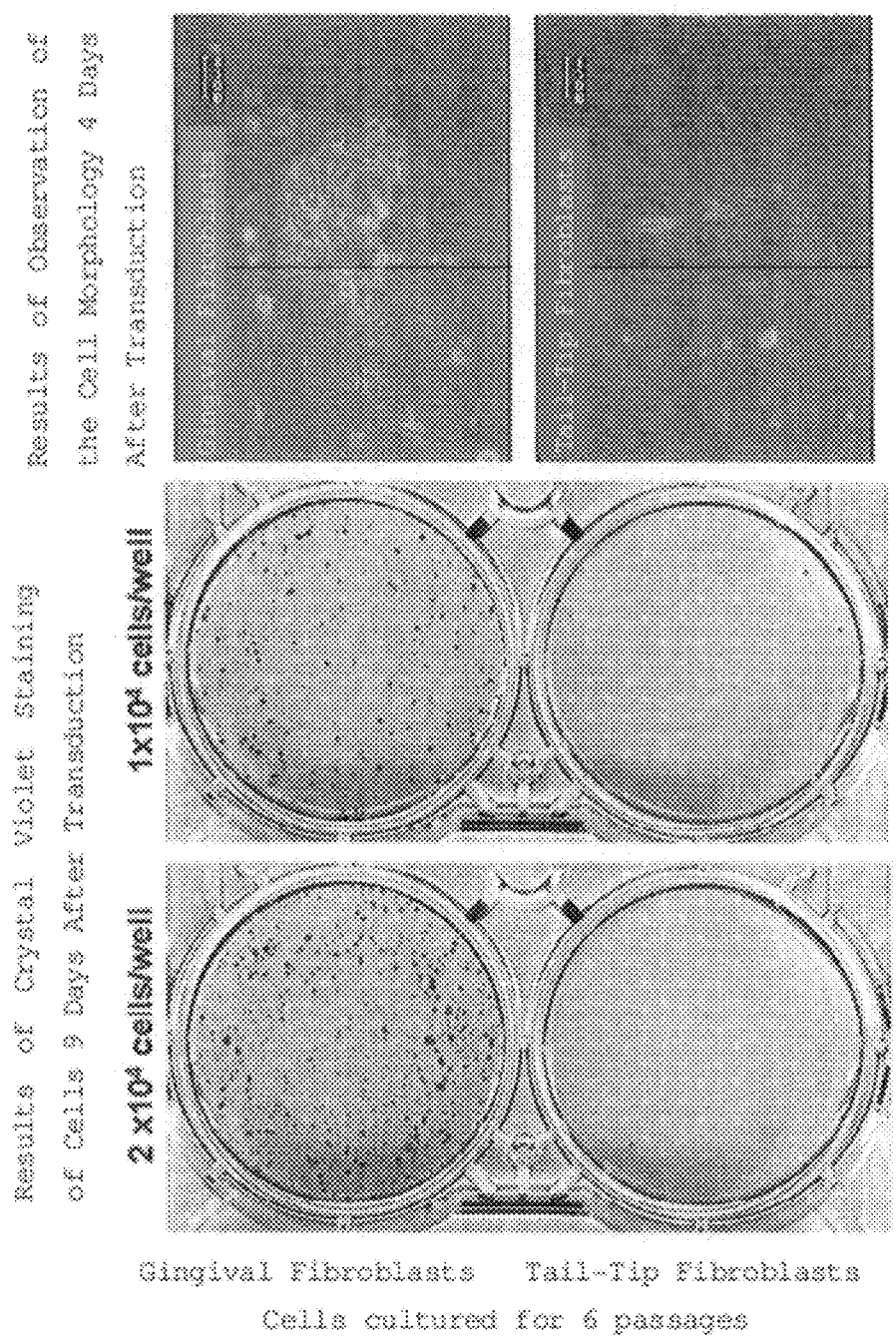
FIG. 4 shows the results obtained in Example 1 by observing the cell morphology 4 days after introducing four factors (c-Myc, Oct3/4, Sox, and Klf4) into mouse gingival fibroblasts and tail-tip fibroblasts after 6 passages.

FIG. 4 shows the results. The results confirmed a significantly greater number of ES cell-like colonies when gingival fibroblasts were used than when tail-tip fibroblasts were used. The above results show that oral mucosal tissue is a source of cells, which enables a rapid and efficient establishment of iPS cells, and that iPS cells established from gingival fibroblasts can be applied to regenerative medical studies in the future.

<In Vitro Differentiation of Gingival Fibroblast-Derived iPS Cells> iPS cells induced from gingival fibroblasts (iPS cells obtained by three-factor transduction: gingival fibroblasts after 6 passages were used for induction) were collected by trypsinization and transferred to low-attachment culture dishes containing ES medium. 3 days later, aggregated cells were seeded into 0.1% gelatin-coated 12-well tissue culture plates or 8-well glass chamber slides (Nalge Nunc International, Naperville, Ill.), and cultured in ES medium for an additional 3 days.

Figure 5:
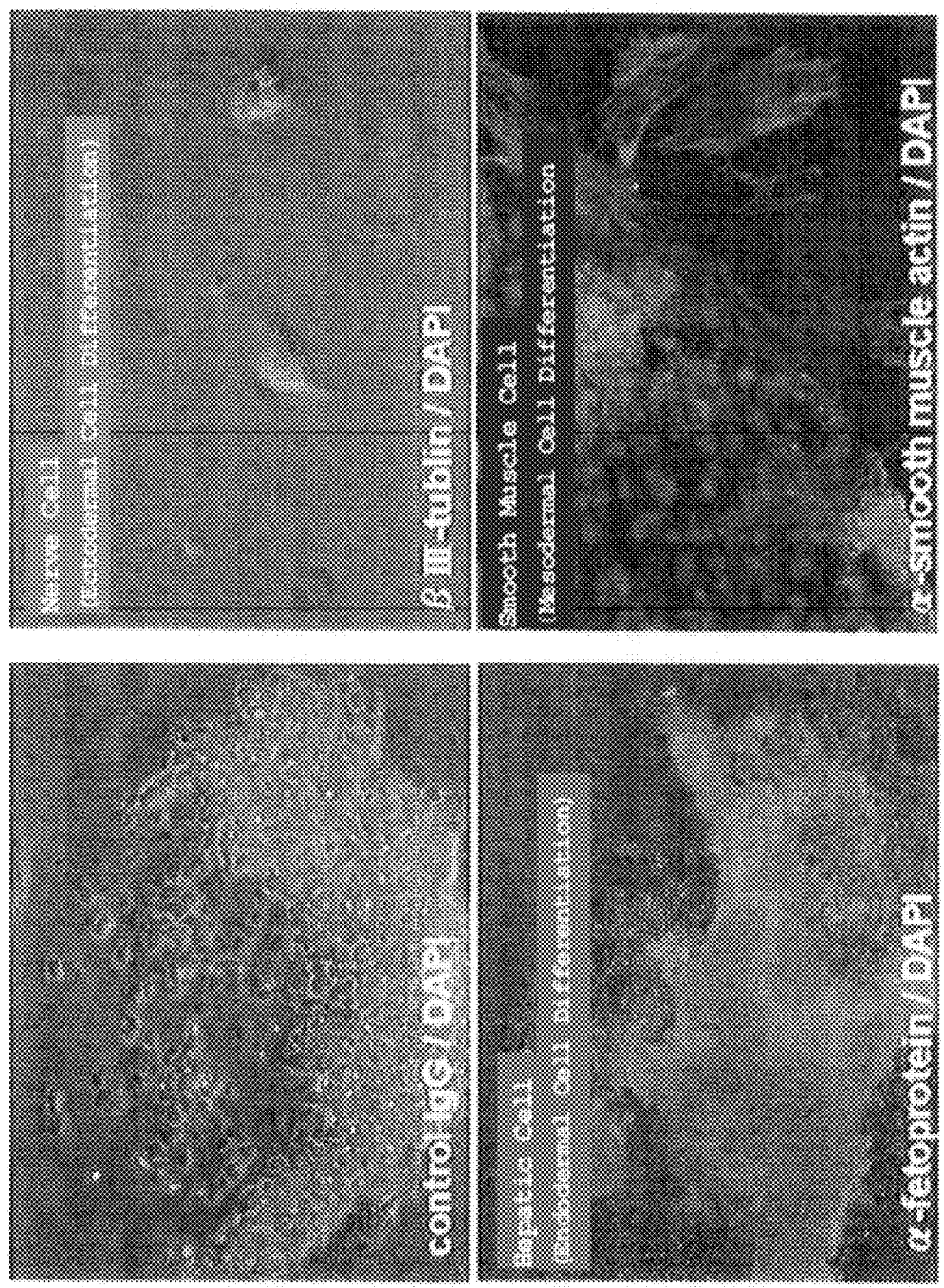
FIG. 5 shows the results obtained in Example 1 by observing the in vitro differentiation potential of iPS cells prepared by introducing three factors (Oct3/4, Sox, and Klf4) into mouse gingival fibroblasts. The upper-left figure shows the results of immunostaining with control IgG (immunoglobulin G) antibody and DAPI nuclear staining; the lower-left figure shows the results of immunostaining with anti-α1-fetoprotein antibody and DAPI nuclear staining; the upper-right figure shows the results of immunostaining with anti-β-III tubulin antibody and DAPI nuclear staining; and the lower-right figure shows the results of immunostaining with anti-α-smooth muscle actin antibody and DAPI nuclear staining.

For fluorescent immunocytostaining, the above cells were fixed with a 10% phosphate buffered formalin solution (Wako Pure Chemical Industries, Ltd., Osaka, Japan), and incubated in a phosphate buffer solution (PBS) containing 1% bovine serum albumin and 0.1% Triton-X100 for 20 minutes. After two washes, the cells were incubated with mouse anti-human α-smooth muscle actin monoclonal antibody (0.05 mol/L; clone 1A4, Dako, Glostrup, Denmark) and rabbit anti-human α1-fetoprotein polyclonal antibody (0.05 mol/L; Dako) at room temperature for 30 minutes; or incubated with mouse anti-human β-III tubulin monoclonal antibody (0.5 µg/ml; clone TU-20, Millipore, Temecula, Calif.) or control IgG (0.5 µg/ml; mouse IgG whole molecules: Santa Cruz Biotechnology, Santa Cruz, Calif.) overnight at 4° C. Subsequently, the cells were washed, and incubated with Alexa 568-goat anti-mouse or anti-rabbit IgG (1:500; Molecular Probes, Eugene, Oreg.) at 37° C. for 30 minutes, followed by DAPI (Roche) nuclear staining. FIG. 5 shows the results. The results confirmed that when the above-prepared iPS cells were cultured in a feeder cell-independent manner, the iPS cells were differentiated, from three germ layer cells, into cells that express β-III (nerve cell), α-fetoprotein (hepatic cell), and α-smooth muscle actin (smooth muscle cell) proteins.

Figure 6:
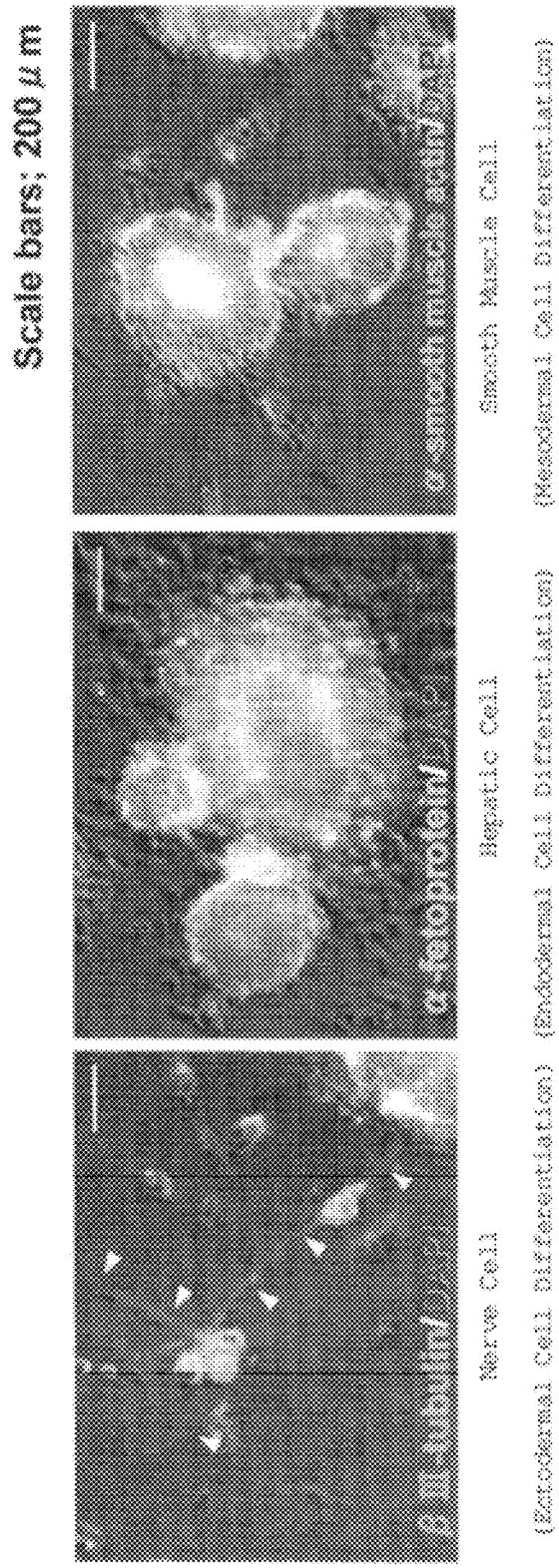
FIG. 6 shows the results obtained in Example 1 by observing the in vitro differentiation potential of iPS cells prepared by introducing four factors (Oct3/4, Sox, Klf4, and c-Myc) into mouse gingival fibroblasts. The left figure shows the results of immunostaining with anti-β-III tubulin antibody and DAPI nuclear staining; the center figure shows the results of immunostaining with anti-α1-fetoprotein antibody and DAPI nuclear staining; and the right figure shows the results of immunostaining with anti-α-smooth actin antibody and DAPI nuclear staining. In the figures, immunostaining with anti-α1-fetoprotein antibody exhibits a green color, and DAPI nuclear staining exhibits a red color.

Further, fluorescent immunostaining was performed under the same conditions described above, using iPS cells induced from gingival fibroblasts (iPS cells obtained by four-factor transduction: gingival fibroblasts after 6 passages were used for induction). FIG. 6 shows the results. The results also confirmed that iPS cells obtained by four-factor transduction were also differentiated, from three germ layer cells, into cells that express β-III tubulin (nerve cell), α-fetoprotein (hepatic cell), and α-smooth muscle actin (smooth muscle cell) proteins.

Figure 7:
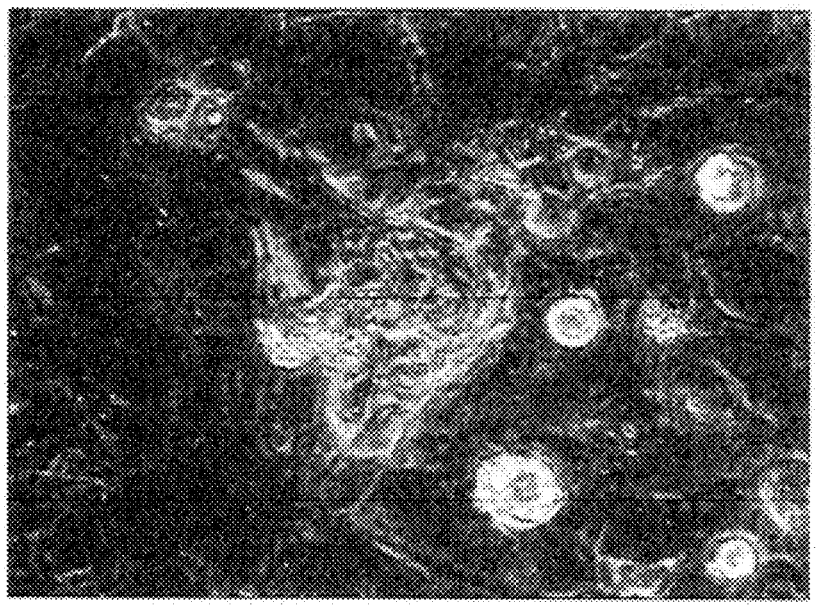
FIG. 7 shows the results obtained in Example 1 by observing in vitro differentiation of iPS cells, which were prepared by introducing three factors (Oct3/4, Sox, and Klf4) into mouse gingival fibroblasts, into beating cells (myocardial cells). The beating of the cells shown in FIG. 7 has been confirmed.

Further, the iPS cell colonies obtained by three-factor transduction (on day 50 after transduction) were seeded onto feeder cells, and cultured for 5 to 10 days in ES medium. As a result, differentiation into beating cells (myocardial cells) was confirmed. FIG. 7 shows the results.

Figure 8:
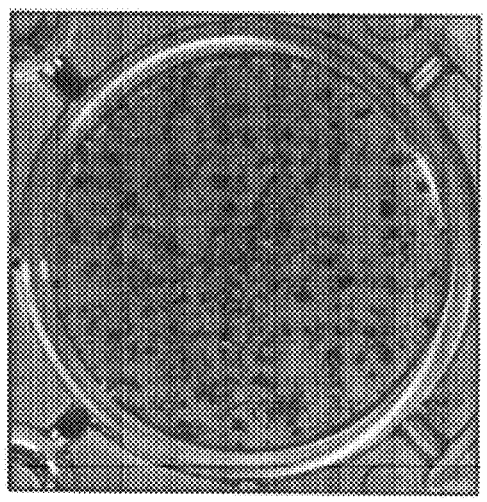
FIG. 8 shows the results obtained in Example 1 in which iPS cells prepared by introducing three factors (Oct3/4, Sox, and Klf4) or four factors (c-Myc, Oct3/4, Sox, and Klf4) into mouse gingival fibroblasts (gingival fibroblasts after 6 passages were used for induction) were cultured for 28 days in bone differentiation induction medium containing dexamethasone, β-glycerophosphoric acid, and ascorbic acid-2-phosphate; and in vitro differentiation of the iPS cells into osteoblasts was observed. The iPS cells prepared by transduction with the three factors (the upper-left figure) and with the four factors (the upper-right figure) were double-stained with alkaline phosphatase and von Kossa. The figures show the results. The lower-left and lower-right figures show enlarged images of the stained cells shown in the upper-right and upper-left figures, respectively. In the figures, the cells that show alkaline phosphatase activity exhibit a red color, and a calcified extracellular matrix exhibits a black color.
Figure 8:
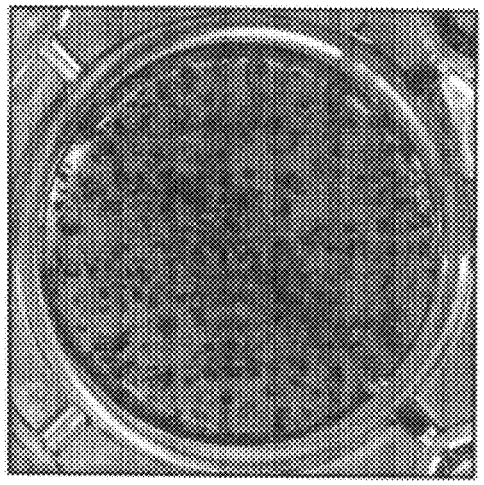
Figure 8:
Figure 8:
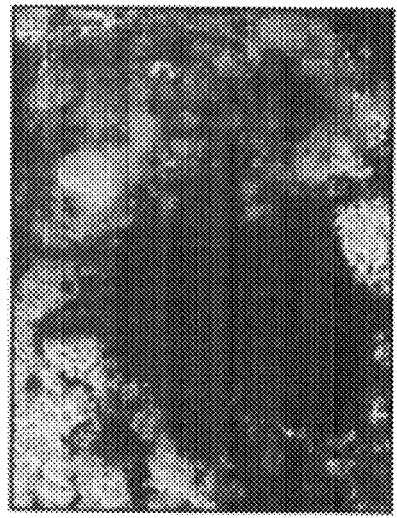

Further, for induction of osteoblast differentiation, iPS cells in 12-well tissue culture plates (iPS cells obtained by three- or four-factor transduction; in either case, gingival fibroblasts after 6 passages were used for induction) were cultured in bone differentiation induction medium containing 0.1 µM dexamethasone, 10 mM β-glycerophosphoric acid, and 50 µM ascorbic acid-2-phosphate (Sigma). The iPS cells were double-stained with alkaline phosphatase and von Kossa in order to detect alkaline phosphatase activity which is an osteoblast markers and calcification of extracellular matrix. FIG. 8 shows the results. The results revealed that the above-prepared iPS cells exhibited alkaline phosphatase activity as well as differentiation potential into calcifying cells (osteoblasts).

<Reverse Transcription Polymerase Chain Reaction (RT-PCR) Analysis>

Total RNA obtained from iPS cells (iPS cells obtained by three- or four-factor transduction: gingival fibroblasts after 6 passages were used for induction) on day 3 after seeding onto feeder cells, mouse ES cells, mouse gingival fibroblasts, and feeder cells used for culturing of iPS cells were used for RT-PCR analysis. Total RNA was extracted using RNeasy Mini Kit (QIAGEN, Hilden, Germany). After DNase I (Ambion, Austin, Tex.) treatment, cDNA was synthesized from 1 µg of total RNA using Super Script III reverse transcriptase (Invitrogen, Carlsbad, Calif.). The cDNA target was amplified by PCR using Taq DNA polymerase (Promega, Madison, Wis.) according to a recommended method. Table 1 below shows PCR primer pairs that were used. PCR products were subjected to 1.5% agarose gel electrophoresis and ethidium bromide staining, and visualized under ultraviolet light illumination (Dolphin-View Image System: Wealtec, Sparks, Nev.). The expression of glyceraldehyde-3-phosphate dehydrogenase (GAPDH) mRNA was used as an internal control.

TABLE 1

Primers used for RT-PCR

| Gene | Primer (Fw, forward; Rv, reverse) |
|---|---|
| Nanog | Fw: 5'-AGG GTC TGC TAC TGA GAT GCT CTG-3' (SEQ ID NO: 1)<br>Rv: 5'-CAA CCA CTG GTT TTT CTG CCA CCG-3' (SEQ ID NO: 2) |
| ERas | Fw: 5'-ACT GCC CCT CAT CAG ACT GCT ACT-3' (SEQ ID NO: 3)<br>Rv: 5'-CAC TGC CTT GTA CTC GGG TAG CTG-3' (SEQ ID NO: 4) |

TABLE 1-continued

Primers used for RT-PCR

| Gene | Primer (Fw, forward; Rv, reverse) |
|---|---|
| Zfp42 (Rex1) | Fw: 5'-ACG AGT GGC AGT TTC TTC TTG GGA-3' (SEQ ID NO: 5)<br>Rv: 5'-TAT GAC TCA CTT CCA GGG GGC ACT-3' (SEQ ID NO: 6) |
| Oct3/4 (endogenous) | Fw: 5'-TCT TTC CAC CAG GCC CCC GGC TC-3' (SEQ ID NO: 7)<br>Rv: 5'-TGC GGG CGG ACA TGG GGA GAT CC-3' (SEQ ID NO: 8) |
| Sox2 (endogenous) | Fw: 5'-TAG AGC TAG ACT CCG GGC GAT GA-3' (SEQ ID NO: 9)<br>Rv: 5'-TTG CCT TAA ACA AGA CCA CGA AA-3' (SEQ ID NO: 10) |
| Klf4 (endogenous) | Fw: 5'-GCG AAC TCA CAC AGG CGA GAA ACC-3' (SEQ ID NO: 11)<br>Rv: 5'-TCG CTT CCT CTT CCT CCG ACA CA-3' (SEQ ID NO: 12) |
| c-Myc (endogenous) | Fw: 5'-TGA CCT AAC TCG AGG AGG AGC TGG AAT C-3' (SEQ ID NO: 13)<br>Rv: 5'-AAG TTT GAG GCA GTT AAA ATT ATG GCT GAA GC-3' (SEQ ID NO: 14) |
| GAPDH | Fw: 5'-CAC CAT GGA GAA GGC CGG GG-3' (SEQ ID NO: 15)<br>Rv: 5'-GAC GGA CAC ATT GGG GGT AG-3' (SEQ ID NO: 16) |

Figure 9:
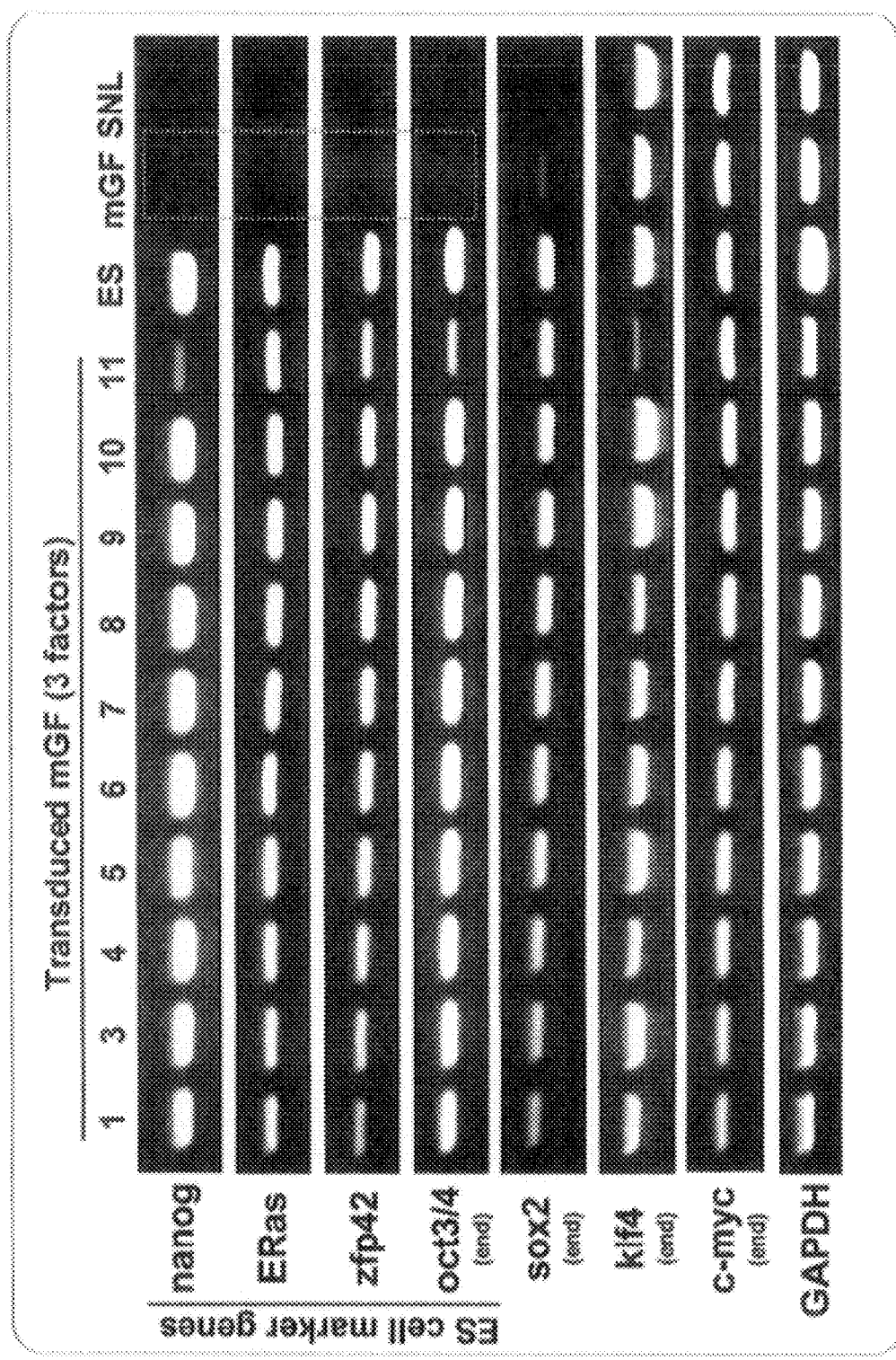
FIG. 9 shows the results obtained in Example 1 by measuring the expression of various marker genes in iPS cells obtained by introducing three factors (Oct3/4, Sox, and Klf4) into mouse gingival fibroblasts (gingival fibroblasts after 6 passages were used for induction); and the expression in mouse ES cells. In the figure, "mGF" refers to mouse gingival fibroblasts, and "SNL" refers to feeder cells used for culturing.
Figure 10:
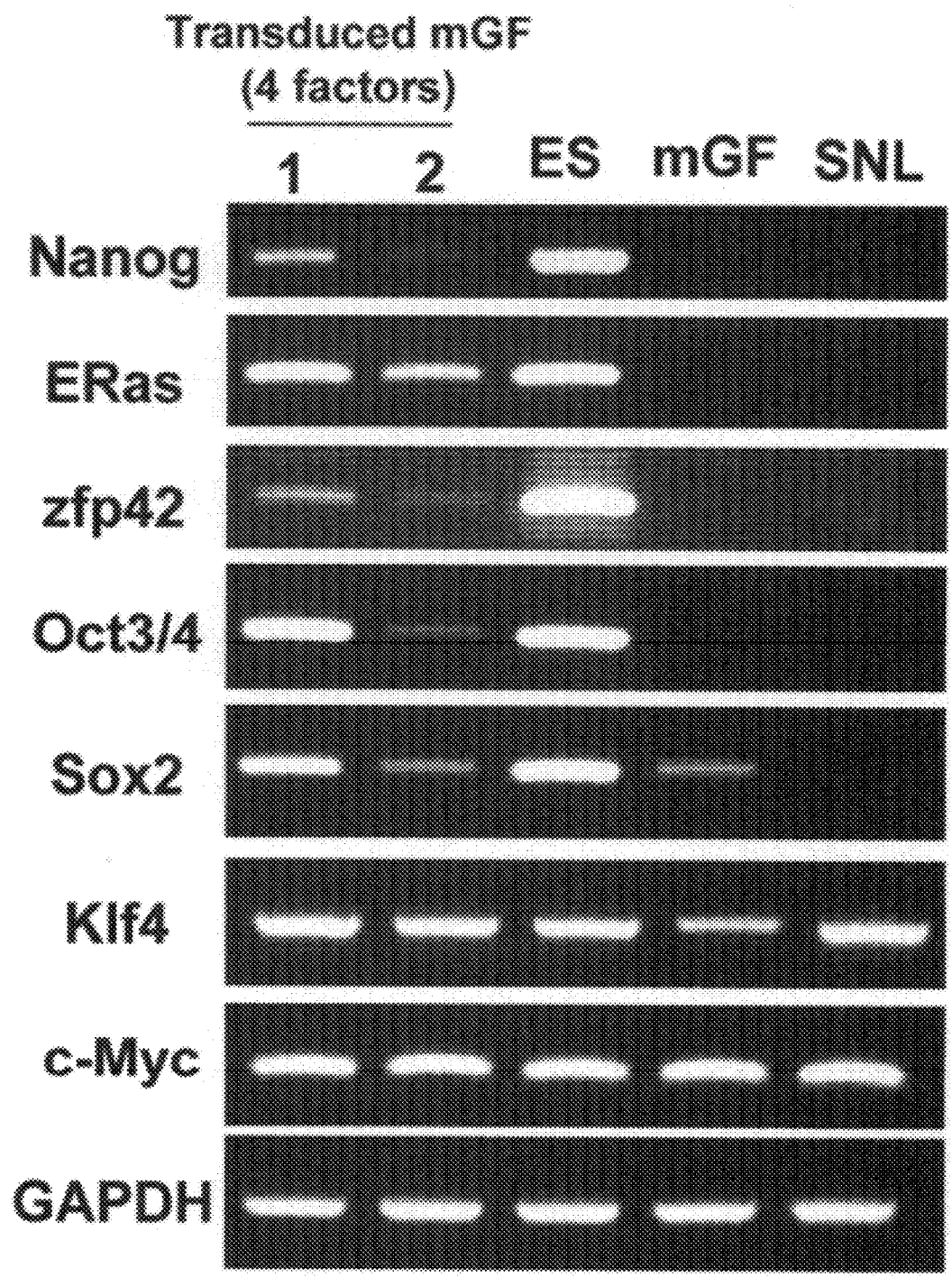
FIG. 10 shows the results obtained in Example 1 by measuring the expression of various marker genes in iPS cells obtained by introducing four factors (c-Myc, Oct3/4, Sox, and Klf4) into mouse gingival fibroblasts (gingival fibroblasts after 6 passages were used for induction); and the expression in mouse ES cells. In the figure, "mGF" refers to mouse gingival fibroblasts, and "SNL" refers to feeder cells used for culturing.

FIGS. 9 and 10 show the obtained results. The results confirmed that iPS cells induced from gingival fibroblasts highly express ES cell-specific marker genes (Nanog, ERas, zfp42, endogenous Oct3/4), and that such iPS cells obtained self-renewal and pluripotency.

<Alkaline Phosphatase Staining> iPS cell clone lines induced for 50 days after three-factor transduction or 20 days after four-factor transduction (gingival fibroblasts after 6 passages were used for induction) were stained with alkaline phosphatase.

Figure 11:
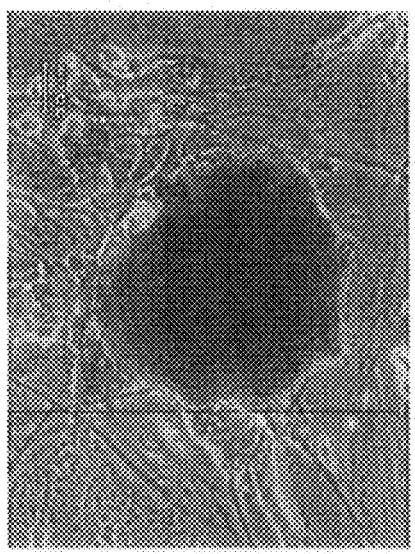
FIG. 11 shows the results obtained in Example 1 by alkaline phosphatase staining of iPS cells obtained by introducing three factors (Oct3/4, Sox, and Klf4) or four factors (c-Myc, Oct3/4, Sox, and Klf4) into mouse gingival fibroblasts (gingival fibroblasts after 6 passages were used for induction).
Figure 11:
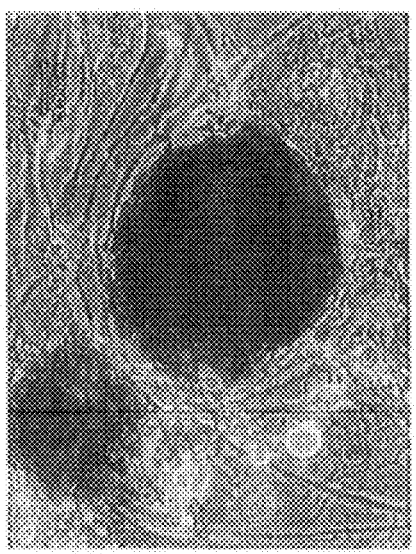
Figure 11:
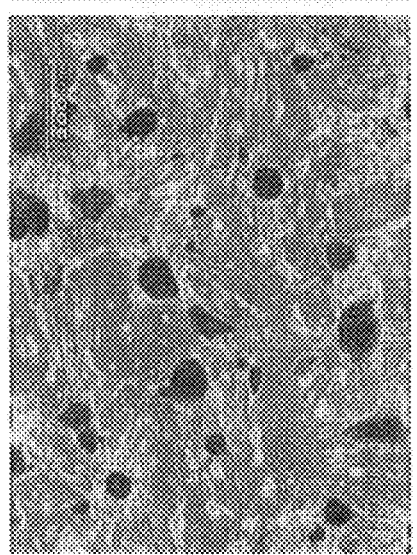
Figure 11:
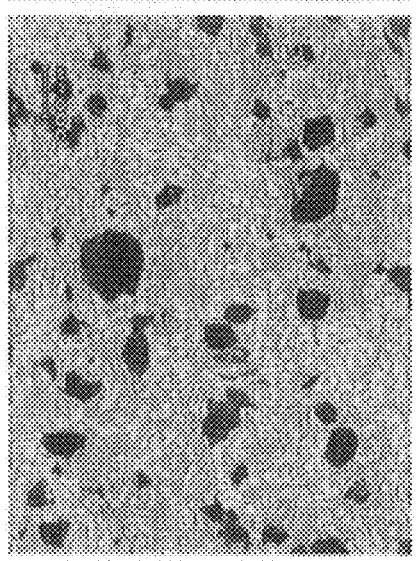
Figure 11:
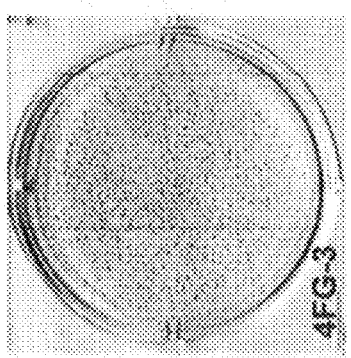
Figure 11:
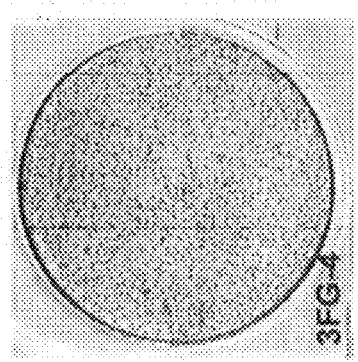

FIG. 11 shows the results. Alkaline phosphatase as an ES cell marker in the above-prepared iPS cells was confirmed to be positive.

<DNA Methylation Analysis> iPS cells (iPS cells obtained by three- or four-factor transduction: gingival fibroblasts after 6 passages were used for induction) and mouse ES cells were cultured free-floating for 3 days. Subsequently, floating aggregated cells (embryoid bodies) were collected, and genomic DNAs were isolated from these aggregated cells and mouse gingival fibroblasts. Using these genomic DNAs, the methylation status of cytosine guanine dinucleotides (CpG) in promoter regions of Nanog and Oct3/4 was analyzed by bisulfite sequencing. Information regarding the promoter regions and CpG loci of Nanog and Oct3/4 was obtained from the database of Transcriptional Start Site (DBTSS Ver. 7.0: see the website having an URL that begins with "http:" and that ends with "//dbtss.h-gc.jp/"). Bisulfite treatment was performed using EpiTect Bisulfite kit (Qiagen). Bisulfite PCR primers shown in Table 2 were used. Amplified products were subcloned into pGEM-T Easy Vector (Promega). Five clones were randomly selected, and DNA base sequence was analyzed with SP6 forward and reverse primers for each PCR amplified product.

TABLE 2

Primers used for Bisulfite PCR

| Gene | Primer (Fw, forward; Rv, reverse) |
|---|---|
| Oct3/4 | Fw: 5'-GGT TTT TTA GAG GAT GGT TGA GTG-3' (SEQ ID NO: 17)<br>Rv: 5'-TCC AAC CCT ACT AAC CCA TCA CC-3' (SEQ ID NO: 18) |
| Nanog | Fw: 5'-GAT TTT GTA GGT GGG ATT AAT TGT GAA TTT-3' (SEQ ID NO: 19)<br>Rv: 5'-ACC AAA AAA ACC CAC ACT CAT ATC AAT ATA-3' (SEQ ID NO: 20) |

Figure 12:
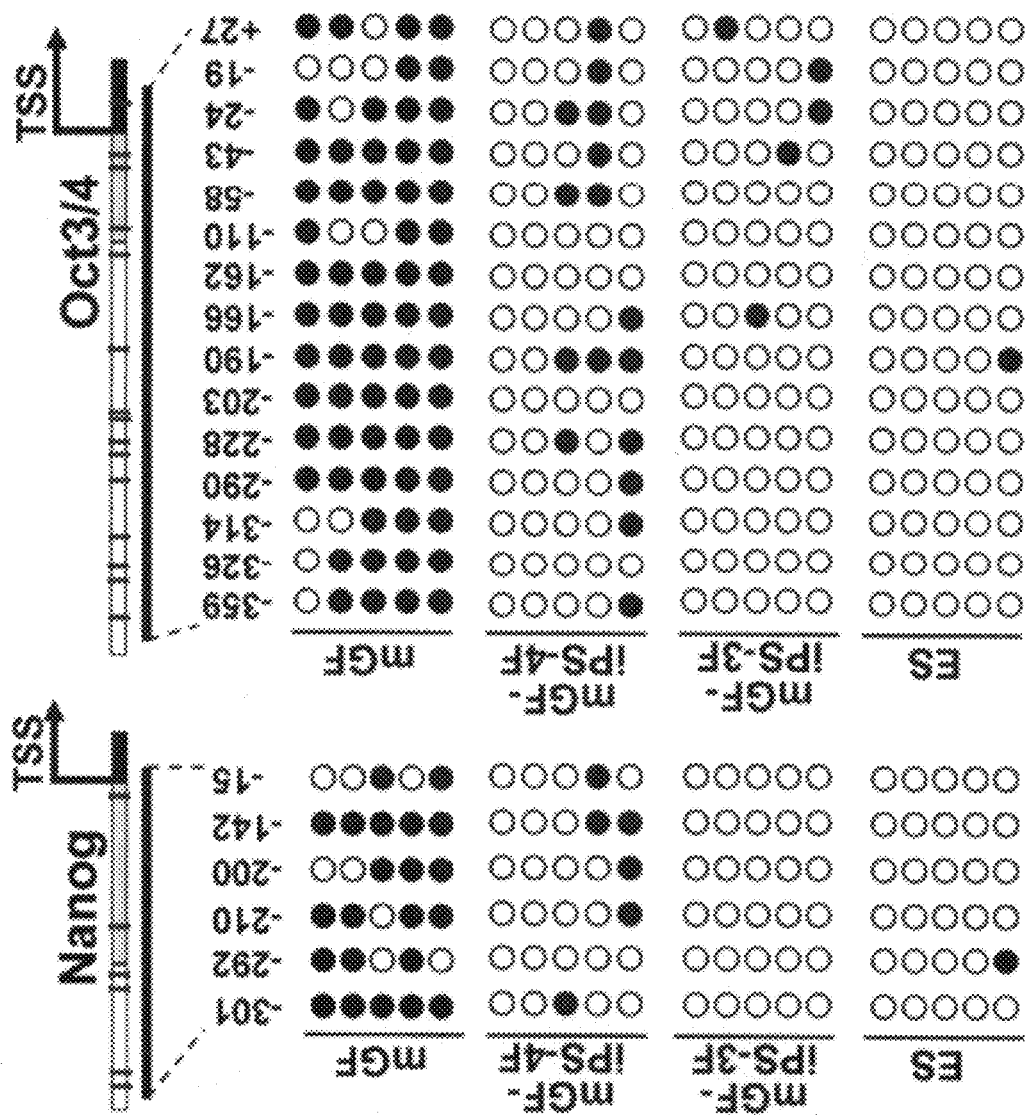
FIG. 12 shows the results obtained in Example 1 by analyzing the methylation status of cytosine guanine dinucleotide (CpG) in the promoter regions of Nanog and Oct3/4 in the following cells: iPS cells (mGF-iPS-3F or 4F) obtained by introducing three factors (Oct3/4, Sox, and Klf4) or four factors (c-Myc, Oct3/4, Sox, and Klf4) into mouse gingival fibroblasts (gingival fibroblasts after 6 passages were used for induction); mouse ES cells; and mouse gingival fibroblasts.

FIG. 12 shows the obtained results. The results reveal that many of the CpGs that had been methylated in the promoter regions of Nanog and Oct3/4 in mouse gingival fibroblasts became demethylated in iPS cells obtained by three- or four-factor transduction. The results also confirmed that the methylation pattern of the promoter regions of Nanog and Oct3/4 in iPS cells obtained by three- or four-factor transduction was similar to that of mouse ES cells. The numerical values shown in FIG. 12 indicate the number of bases from the transcriptional start site of each gene to each CpG site. The gray regions indicate untranslated regions, and the black regions indicate translated regions.

It became clear from the above results that the promoter regions of Nanog and Oct3/4 in iPS cells obtained by three- or four-factor transduction were demethylated, and the expression of these genes was in a state of being promoted, as is the case with ES cells.

<Teratoma Formation and Histological Analysis>

Eight-week old SCID mice (C.B-17; Clea Japan, Tokyo, Japan) were anesthetized with diethyl ether and a 1:10 dilution of Nembutal (Dainippon Sumitomo Pharmaceutical, Osaka, Japan) by intraperitoneal administration (0.1 ml per 100 g body weight). A cell suspension (0.2 to $0.5 \times 10^6$ cells/testis) in which iPS cells (iPS cells obtained by three- or four-factor transduction: 3 passages) were suspended in cold Hank's balanced salt solution (Gibco) was injected in an amount of 20 μl into the medulla of mouse testes using a Hamilton syringe. The mice were thereafter housed with free access to water and food under specific pathogen-free conditions. After 7 to 10 weeks, the mice were perfused with PBS, and then perfused with a fixative solution containing 1% paraformaldehyde and 1.25% glutaraldehyde. Teratomas formed in the mouse testes were excised for histological analysis. Specimens were embedded in paraffin and sectioned at 3 μm thickness for hematoxylin and eosin (H&E) staining.

Figure 13:
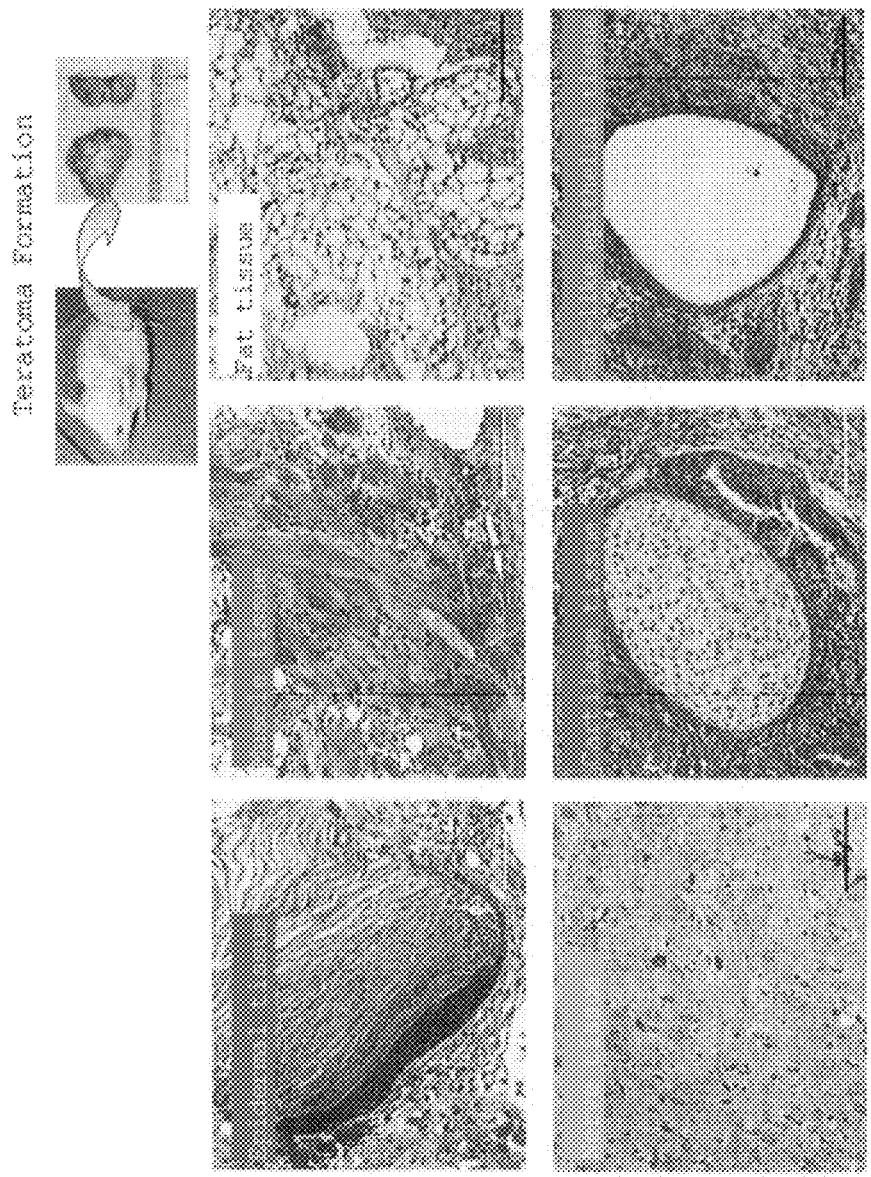
FIG. 13 shows the results obtained in Example 1 in which iPS cells obtained by introducing three factors (Oct3/4, Sox, and Klf4) into mouse gingival fibroblasts (gingival fibroblasts after 6 passages were used for induction) were injected into the medulla of mouse testes; and teratomas formed after the injection were histologically analyzed by hematoxylin and eosin staining.
Figure 14:
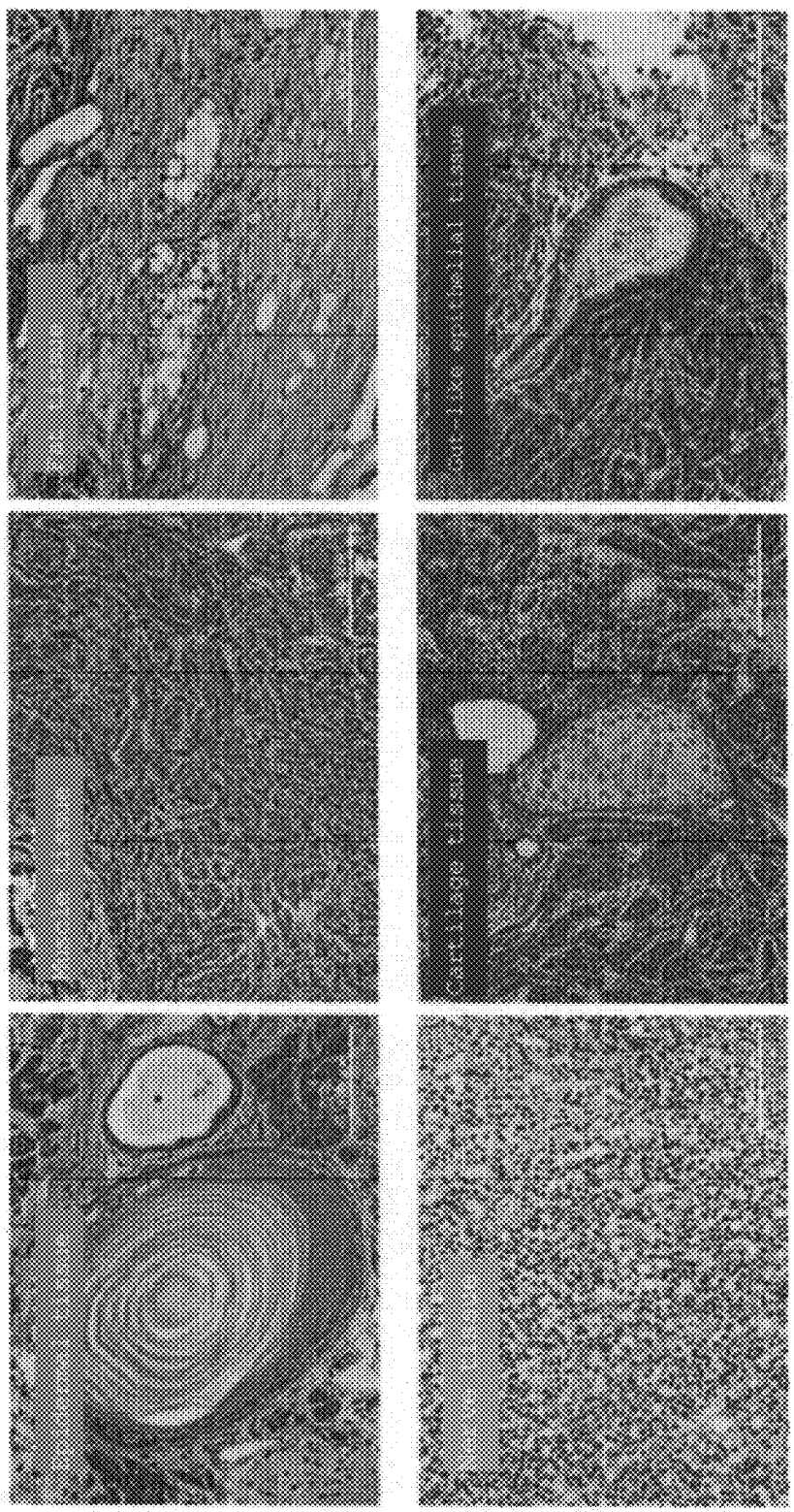
FIG. 14 shows the results obtained in Example 1 in which iPS cells obtained by introducing four factors (c-Myc, Oct3/4, Sox, and Klf4) into mouse gingival fibroblasts (gingival fibroblasts after 6 passages were used for induction) were injected into the medulla of mouse testes; and teratomas formed after the injection were histologically analyzed by hematoxylin and eosin staining.

FIGS. 13 and 14 show the results of H&E staining. According to the results, images of tissues such as epidermal tissue, muscle tissue, fat tissue, nerve tissue, cartilage tissue, and gut-like epithelial tissue were observed in the medulla of SCID mouse testes injected with the above-prepared iPS cells. The results confirmed a differentiation potential of the above-prepared iPS cells into various tissues derived from three germ layers.

<Reprogramming Efficiency Analysis>

In order to compare the reprogramming efficiency (iPS cell induction efficiency) between gingival fibroblasts and tail-tip fibroblasts, gingival tissue and tail tissue were collected from the same male 10-week old C57BL/6J mouse, and gingival fibroblasts and tail-tip fibroblasts were obtained under the same conditions described above. The thus-obtained gingival fibroblasts and tail-tip fibroblasts were continued to be subcultured in FP medium (DMEM (Dulbecco's modified Eagle medium without sodium pyruvate: Nacalai Tesque, Kyoto) medium containing 10% fetal bovine serum (Sigma, St. Louis, Mo.), 50 units/ml penicillin, and 50 μg/ml streptomycin)).

Gingival fibroblasts and tail-tip fibroblasts after 4, 7, and 10 passages were induced into iPS cells by transduction with four factors (Oct3/4, Sox, Klf4, and c-Myc) under the same conditions described above. Induction into iPS cells was confirmed by the observation of ES cell-like morphology and alkaline phosphatase staining. The reprogramming efficiency into iPS cells was calculated as a percentage (%) of the number of iPS cell colonies relative to the number of cells used for transformation.

Figure 15:
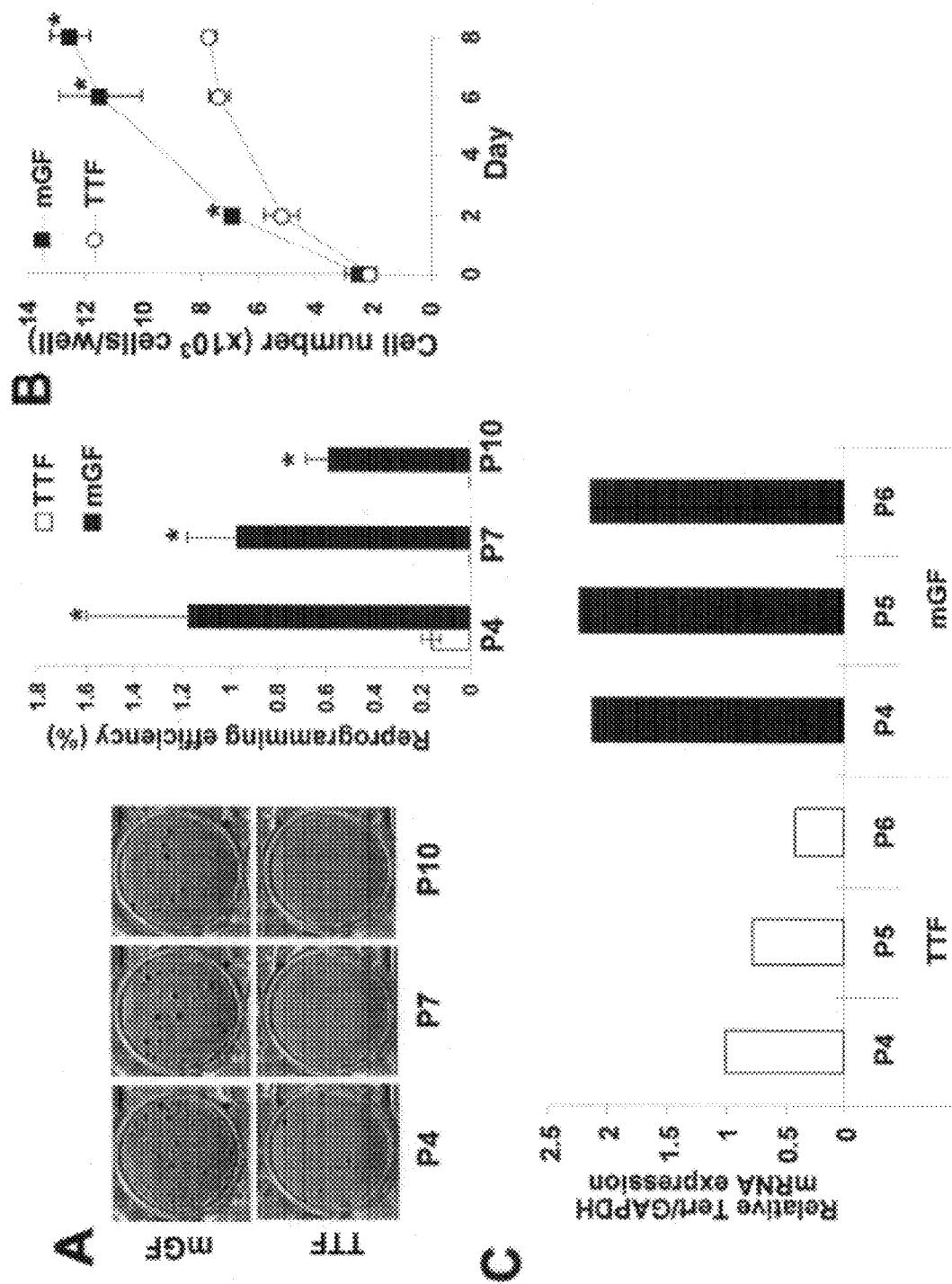
FIG. 15 shows the results obtained in Example 1 by evaluating the reprogramming efficiency (iPS cell induction efficiency) in mouse gingival fibroblasts (mGF) and mouse tail-tip fibroblasts (TTF).

FIG. 15A shows the obtained results. The image on the left in FIG. 15A shows the results of alkaline phosphatase staining after introducing the four factors into each cell to induce the cells into iPS cells. Further, the graph on the right in FIG. 15A shows the reprogramming efficiency when iPS cells were induced from cells after 4, 7, and 10 passages. These results confirmed that introduction of the four factors into tail-tip fibroblasts was hardly able to induce iPS cells after tail-tip fibroblasts were cultured for 7 and 10 passages. In contrast, introduction of the four factors into gingival fibroblasts was able to efficiently induce iPS cells even after gingival fibroblasts were cultured for 10 passages.

Further, in order to compare growth characteristics between gingival fibroblasts and tail-tip fibroblasts, these cells were added at $2 \times 10^3$ cells per well of 96-well plates to which 100 μl/well of FP medium (DMEM (Dulbecco's modified Eagle medium without sodium pyruvate: Nacalai Tesque, Kyoto) medium containing 10% fetal bovine serum (Sigma, St. Louis, Mo.), 50 units/ml penicillin, and 50 μg/ml streptomycin)) was added. The cells were cultured at 37° C. with 5% $CO_2$ for 8 days, and the number of cells was measured using WST-1 cell counting assay (Dojindo Laboratories, Kumamoto) on day 2, day 6, and day 8. FIG. 15B shows the results.

The results revealed that gingival fibroblasts exhibit significantly higher proliferation potential, compared to tail-tip fibroblasts.

Further, cells after 4, 5, and 6 passages were subjected to real-time RT-PCR analysis for endogenous expression of Tert required for maintenance of telomere that contributes to cell proliferation. TaqMan probes and primers (Mm00436931_m1: Applied Biosystems) were used for the analysis. With respect to the mRNA expression level of each gene in tail-tip fibroblasts cultured for 4 passages, the relative mRNA expression level of corresponding Tert was determined using GAPDH (4352339E: Applied Biosystems) as an internal control. FIG. 15C shows the results. As is clear from FIG. 15C, the expression level of Tert mRNA was maintained in gingival fibroblasts even after 6 passages; however, the expression level of Tert mRNA in tail-tip fibroblasts decreased along with the increase in the number of passages. The above analysis results of the gene expression level also support the fact that gingival fibroblasts have higher proliferation potential, compared to tail-tip fibroblasts.

Example 2

Preparation and Evaluation of Human iPS Cells iPS cells were induced from human gingival fibroblasts with the experimental materials and conditions described below, and the properties of induced iPS cells were evaluated.

<Isolation and Culture of Human Gingival Fibroblasts>

Figure 16:
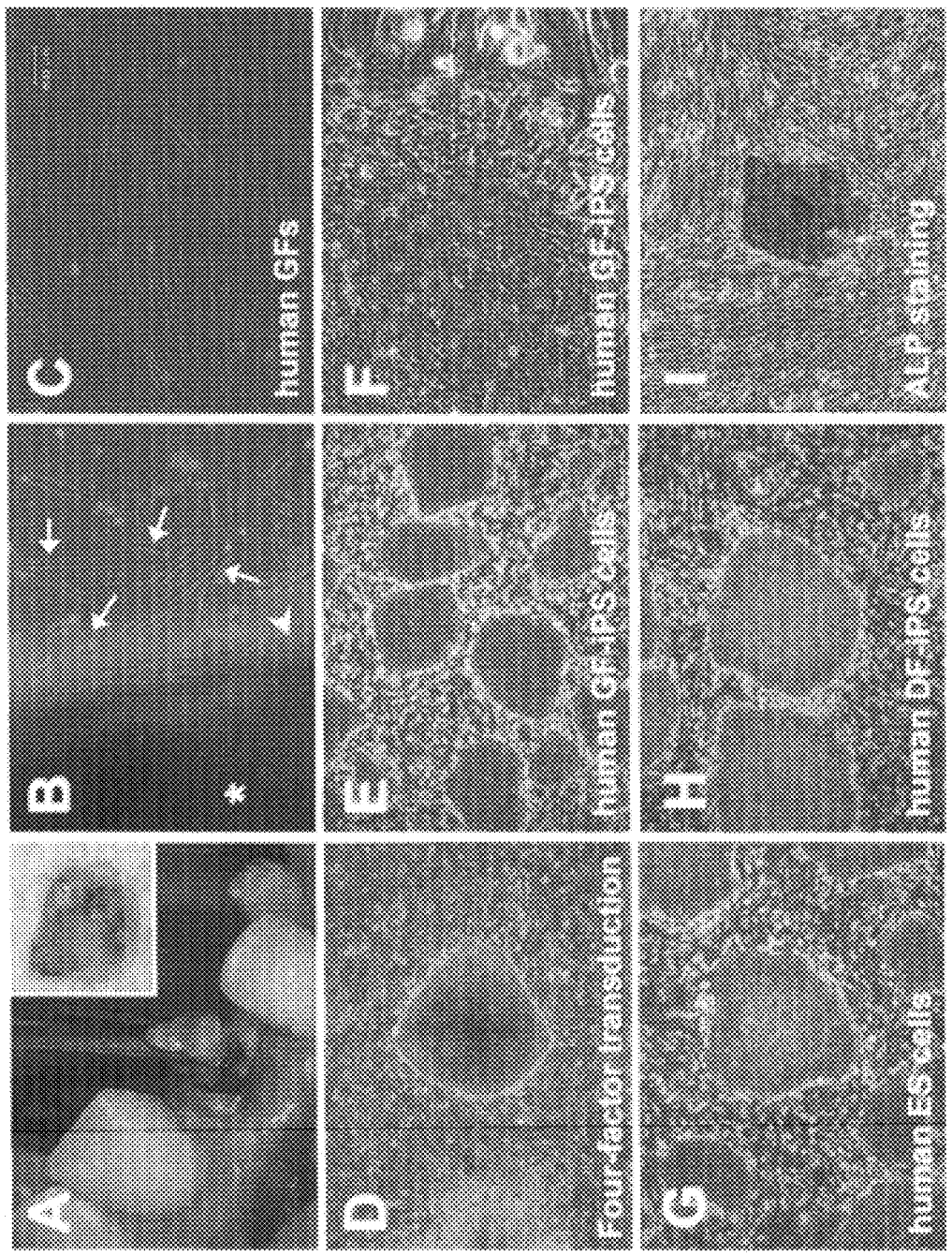
FIG. 16 shows test materials used in Example 2 when inducing iPS cells from human gingival fibroblasts; and the results obtained by observing cells obtained in each stage.

In accordance with a protocol approved by the Institutional Review Board at Osaka University School of Dentistry, healthy human gingival tissue fragments were obtained from a 24-year old man by excision during dental implant surgery (see FIG. 16A). The human gingival tissue fragments were minced and closely attached to 0.1% gelatin-coated tissue culture plates, followed by standing at 37° C. with 5% $CO_2$, with FP medium (DMEM (Dulbecco's modified Eagle medium without sodium pyruvate: Nacalai Tesque, Kyoto) medium containing 10% fetal bovine serum (Sigma, St. Louis, Mo.), 50 units/ml penicillin, and 50 μg/ml streptomycin)) added to the plates to cover the tissue fragments. Thereby, gingival fibroblasts and gingival epithelial cells were grown (see FIG. 16B). In FP medium, epithelial cells undergo differentiation, stop proliferation, and are peeled off. Therefore, by using this medium for subculture, homogeneous human gingival fibroblasts were obtained (see FIG. 16C).

<iPS Cells Induced from Human Embryonic Stem (ES) Cell Lines and Human Dermal Fibroblasts> iPS cells established from human dermal fibroblasts, human embryonic stem (ES) cell line (KhES-1; the number of passages: 35), and human dermal fibroblasts were obtained from the Institute for Frontier Medical Sciences, Kyoto University. Human ES cells were handled in accordance with the guidelines for utilization of human ES cells established by the Ministry of Education, Culture, Sports, Science and Technology, Japan. SNL feeder cells obtained from Dr. Allan Bradley (Sanger Institute, London, UK) were used.

<Production of Retrovirus Particles>

For four-factor transduction via retroviral infection, expression of a lentiviral vector for expression of mouse Slc7a1 (pLenti6/UbC/mSlc7a1 vector) was induced in advance in human gingival fibroblasts and human dermal fibroblasts. In this respect, first, $4 \times 10^6$ 293FT cells (Invitrogen) were seeded into 10-cm culture plates in 293FT medium (DMEM medium containing 10% fetal bovine serum (Sigma, St. Louis, Mo.), 2 mM L-glutamine (Invitrogen), 1×10$^{-4}$ M non-essential amino acids (Invitrogen), 1 mM sodium pyruvate (Sigma), 50 units/ml penicillin, and 50 μg/ml streptomycin (Invitrogen) (Nacalai Tesque)). On the following day, 3 μg of pLenti6/UbC/mSlc7a1 vector (purchased from Addgene) was introduced into 293FT cells using a mixture solution of ViraPower Lentiviral expression system (Invitrogen) or Lipofectamine 2000 (Invitrogen) and OPTI-MEMI medium (Invitrogen). Twenty-four hours after gene transfection, the 293FT medium was replaced with fresh 293FT medium, and the culture supernatant was collected 24 hours after the replacement.

Meanwhile, 8×10$^5$ human gingival fibroblasts and human dermal fibroblasts were seeded into 10-cm culture plates in FP medium the day before lentiviral infection. Medium of human gingival fibroblasts and human dermal fibroblasts was replaced with culture supernatant containing collected lentiviral particle, to which polybrene (final concentration: 4 μg/ml) was added. Cells were thereby infected with a lentivirus, and cultured overnight at 37° C. with 5% $CO_2$. The medium was replaced with FP medium 24 hours after infection, and each cell in the FP medium was used for the next retroviral infection.

Retroviral vectors (pMXs) containing human c-Myc, Oct3/4, Sox2 or Klf4 (cDNA) were purchased from Addgene (Cambridge, Mass.). Platinum-E packaging cells supplied by Dr. Toshio Kitamura at the University of Tokyo were used to produce virus particles.

Each plasmid vector (9 μg) was mixed with a mixture solution of OPTI-MEMI medium (Invitrogen) and FuGENE 6 reagent (Roche, Basel, Switzerland), and the mixture was transfected into Platinum-E cells by the lipofection method. The culture supernatant containing each virus particle was collected 48 hours after gene transfection, and used for retroviral infection (iPS cell induction) of gingival fibroblasts or dermal fibroblasts.

<iPS Cell Induction>

Twenty-four hours before transduction by retroviral infection, gingival fibroblasts or human dermal fibroblasts were seeded at 8×10$^5$ cells into 0.1% gelatin-coated 10-cm culture plates, and cultured in FP medium (DMEM (Dulbecco's modified Eagle medium without sodium pyruvate: Nacalai Tesque, Kyoto) medium containing 10% fetal bovine serum (Sigma, St. Louis, Mo.), 50 units/ml penicillin, and 50 μg/ml streptomycin)). iPS cells were induced using four factors (c-Myc, Oct3/4, Sox, and Klf4). For iPS cell induction, the supernatant containing each virus of the four factors was mixed in such a manner that the factors would ultimately be present in equal amounts. The culture medium of each fibroblast was replaced with a solution which is the above mixture supplemented with polybrene (final concentration: 4 μg/ml), and the cells were cultured overnight at 37° C. with 5% $CO_2$. For 5 days from the following day, the culture supernatant was removed every day by suction, and replaced with fresh FP medium. Six days after retroviral infection, 5×10$^4$ cells for fibroblast were seeded onto mitomycin C-inactivated SNL feeder cells (1.5×10$^6$) seeded into 10-cm culture plates. On the following day, the medium was replaced with Primate ES medium (ReproCELL); and thereafter, the medium was replaced with fresh medium once every two days. Several colonies exhibiting ES cell-like morphology, which emerged 15 to 26 days after transduction, were selected and subcultured. Among the colonies that were cloned, cell lines derived from colonies of cells particularly exhibiting ES cell-like morphology and proliferation potential were regarded as iPS cells.

The thus-obtained human gingival fibroblasts transduced with the four factors formed iPS cell-like colonies (see 16D). In contrast, hardly any iPS cell-like colonies were formed in dermal fibroblasts transduced with the four factors under the same conditions. Further, 26 days after transduction, iPS cell-like colonies derived from human gingival fibroblasts were mechanically picked and subcultured, thereby obtaining 5 clone lines (see FIGS. 16E and 16F). The colonies grew, and exhibited the same morphology and growth characteristics as those of iPS cells (see FIG. 16H) established from human ES cells (see FIG. 16G) and human dermal fibroblasts. Further, ES cell-like colonies induced from human gingival fibroblasts were also confirmed to show strong alkaline phosphatase activity, which is regarded as an ES cell marker (see FIG. 16I).

The above results confirmed that human iPS cells can be more efficiently established from human gingival fibroblasts than from human dermal fibroblasts.

<Reverse Transcription Polymerase Chain Reaction (RT-PCR) Analysis>

RT-PCR analysis was performed using total RNA obtained from the thus-obtained 5 clone lines of iPS cell (iPS cells obtained by introducing the four factors into human gingival fibroblasts), human ES cells, human gingival fibroblasts, and feeder cells used for culturing iPS cells. RT-PCR analysis was performed by the same method as in Example 1, using the primers shown in Table 3.

TABLE 3

Primers used for RT-PCR

| Gene | Primer (Fw, forward; Rv, reverse) |
|---|---|
| NANOG | Fw: 5'-CAG CCC CGA TTC TTC CAC CAG TCC C-3' (SEQ ID NO: 21) Rv: 5'-CGG AAG ATT CCC AGT CGG GTT CAC C-3' (SEQ ID NO: 22) |
| OCT3/4 (endogenous) | Fw: 5'-GAC AGG GGG AGG GGA GGA GCT AGG-3' (SEQ ID NO: 23) Rv: 5'-CTT CCC TCC AAC CAG TTG CCC CAA AC-3' (SEQ ID NO: 24) |
| SOX2 (endogenous) | Fw: 5'-GGG AAA TGG GAG GGG TGC AAA AGA GG-3' (SEQ ID NO: 25) Rv: 5'-TTG CGT GAG TGT GGA TGG GAT TGG TG-3' (SEQ ID NO: 26) |
| REX1 | Fw: 5'-CAG ATC CTA AAC AGC TCG CAG AAT-3' (SEQ ID NO: 27) Rv: 5'-GCG TAC GCA AAT TAA AGT CCA GA-3' (SEQ ID NO: 28) |
| GAPDH | Fw: 5'-GTC AAG GCC GAG AAT GGG AA-3' (SEQ ID NO: 29) Rv: 5'-GCT TCA CCA CCT TCT TGA TG-3' (SEQ ID NO: 30) |

Figure 17:
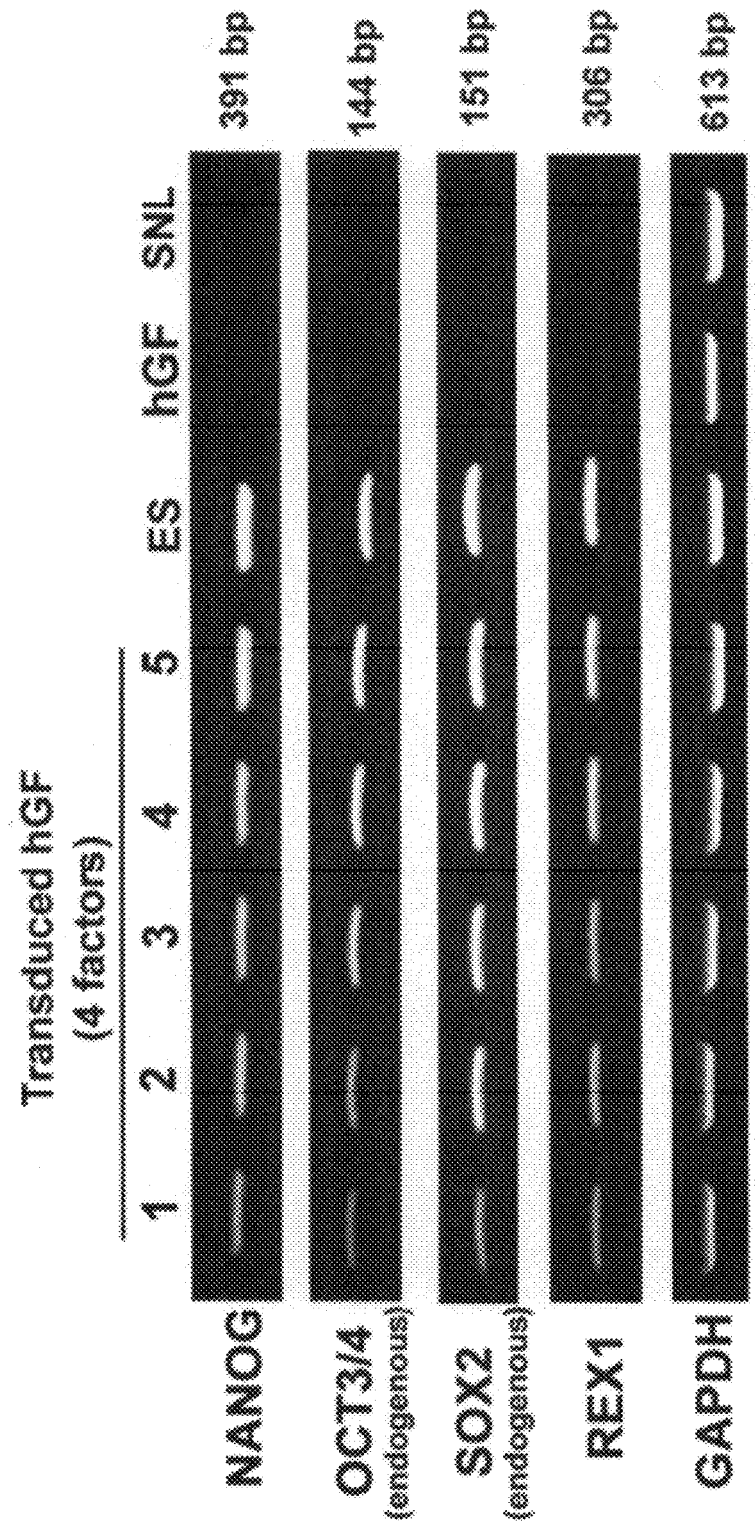
FIG. 17 shows the results obtained in Example 2 by measuring the expression of various marker genes in iPS cells (transduced hGF) prepared by introducing four factors (c-Myc, Oct3/4, Sox, and Klf4) into human gingival fibroblasts; and the expression in human ES cells. In the figure, "hGF" refers to human gingival fibroblasts, and "SNL" refers to feeder cells used for culturing.

FIG. 17 shows the obtained results. The results confirmed that iPS cells induced from human gingival fibroblasts highly express ES cell-specific marker genes (NANOG, endogenous OCT3/4, endogenous SOX2, and REX1), and that such iPS cells have obtained self-renewal and pluripotency.

The invention claimed is:

1. A method for producing mouse or human induced pluripotent stem cells, comprising a step of introducing a vector encoding reprogramming factors Oct 3/4, Sox2, and Klf4 into mouse or human gingival fibroblasts, wherein expression of the reprogramming factors in the gingival fibroblasts induces reprogramming of said gingival fibroblasts into pluripotent stem cells, thereby producing mouse or human induced pluripotent stem cells.

2. The production method according to claim 1, wherein the reprogramming factors further comprise a Myc family gene.

* * * * *